US007429248B1

(12) United States Patent
Winder et al.

(10) Patent No.: US 7,429,248 B1
(45) Date of Patent: Sep. 30, 2008

(54) METHOD AND APPARATUS FOR CONTROLLING ACOUSTIC MODES IN TISSUE HEALING APPLICATIONS

(75) Inventors: Alan A. Winder, Westport, CT (US); Roger J. Talish, Hillsborough, NJ (US)

(73) Assignee: Exogen, Inc., Piscataway, NJ (US)

( * ) Notice: Subject to any disclaimer, the term of this patent is extended or adjusted under 35 U.S.C. 154(b) by 1423 days.

(21) Appl. No.: 09/925,193

(22) Filed: Aug. 9, 2001

(51) Int. Cl.
*A61H 1/00* (2006.01)
(52) U.S. Cl. .......................................................... 601/2
(58) Field of Classification Search ................. 601/2–4; 600/642, 644, 407–480
See application file for complete search history.

(56) References Cited

U.S. PATENT DOCUMENTS

| | | |
|---|---|---|
| 1,063,782 A | 6/1913 | Dickey |
| 1,604,870 A | 10/1926 | Asman |
| 2,914,829 A | 12/1959 | Willemain |
| 2,920,853 A | 1/1960 | Bufogle |
| 3,117,571 A | 1/1964 | Fry et al. |
| 3,134,451 A | 5/1964 | Hanssen |
| 3,193,034 A | 7/1965 | Hutchinson et al. |
| 3,241,375 A | 3/1966 | Canzoneri |
| 3,304,036 A | 2/1967 | Davis |
| 3,310,049 A | 3/1967 | Clynes |
| 3,433,663 A | 3/1969 | Underwood |
| 3,499,437 A | 3/1970 | Balamuth |
| 3,521,225 A | 7/1970 | Kursman et al. |
| 3,550,586 A | 12/1970 | Balamuth |
| 3,575,050 A * | 4/1971 | Lynnworth ................ 73/861.27 |
| 3,594,993 A | 7/1971 | Heyse |
| 3,664,626 A | 5/1972 | Sneller |
| 3,701,352 A | 10/1972 | Bosworth |
| 3,714,619 A | 1/1973 | Morgan et al. |

(Continued)

FOREIGN PATENT DOCUMENTS

AU         19950292         2/2000

(Continued)

OTHER PUBLICATIONS

Photographs of Vibrations Platform Built by Julio Tous, Univiersitat Ramon Llluli, Barcelona, Spain (7 pages, 2002).

(Continued)

*Primary Examiner*—Brian L. Casler
*Assistant Examiner*—Nasir Shahrestani
(74) *Attorney, Agent, or Firm*—Kilpatrick Stockton LLP (57) ABSTRACT

A modal converter having at least one ultrasonic transducer or at least one array of such transducers positioned on the modal converter at various angles relative to a tissue surface and bone tissue surface, such that some combination of one or more of the following occur: longitudinal waves are produced perpendicular to the bone surface, longitudinal waves propagate along the surface of the skin after incidence at the skin tissue surface, and both longitudinal and shear waves propagate along the surface of the bone after incidence at the bone tissue surface. Illuminating an open tissue wound and bone fracture site with these acoustic modes enhances and promotes angiogenesis and the biological endostial or periostial healing phases, or both, of the bone fracture healing process. The spatial and temporal distribution of acoustic waves directed to the treatment area via the ultrasonic transducers and the modal converter may be controlled.

70 Claims, 5 Drawing Sheets

U.S. PATENT DOCUMENTS

| | | |
|---|---|---|
| 3,729,162 A | 4/1973 | Salvato |
| 3,760,799 A | 9/1973 | Crowson |
| 3,767,195 A | 10/1973 | Dimick |
| 3,828,769 A | 8/1974 | Mettler |
| 3,855,638 A | 12/1974 | Pilliar |
| 3,890,953 A | 6/1975 | Kraus et al. |
| 3,961,380 A | 6/1976 | Garr |
| 3,986,212 A | 10/1976 | Sauer |
| 4,037,592 A | 7/1977 | Kronner |
| 4,105,017 A | 8/1978 | Ryaby et al. |
| 4,108,165 A | 8/1978 | Kopp et al. |
| 4,127,125 A | 11/1978 | Takemoto et al. |
| 4,141,524 A | 2/1979 | Corvese, Jr. |
| 4,164,794 A | 8/1979 | Spector et al. |
| 4,170,045 A | 10/1979 | Estes |
| 4,176,664 A | 12/1979 | Talish |
| 4,195,517 A * | 4/1980 | Kalinoski et al. ........ 73/861.27 |
| 4,206,516 A | 6/1980 | Pilliar |
| 4,216,766 A | 8/1980 | Duykers et al. |
| 4,227,111 A | 10/1980 | Cross et al. |
| 4,229,992 A | 10/1980 | McKee et al. |
| 4,233,477 A | 11/1980 | Rice et al. |
| 4,266,532 A | 5/1981 | Ryaby et al. |
| 4,266,533 A | 5/1981 | Ryaby et al. |
| 4,269,797 A | 5/1981 | Mikiya et al. |
| 4,291,025 A | 9/1981 | Pellico |
| 4,296,753 A | 10/1981 | Goudin |
| 4,312,536 A | 1/1982 | Lloyd |
| 4,315,503 A | 2/1982 | Ryaby et al. |
| 4,315,514 A | 2/1982 | Drewes et al. |
| 4,347,645 A | 9/1982 | Iseki |
| 4,351,069 A | 9/1982 | Ballintyn et al. |
| 4,355,428 A | 10/1982 | Deloison et al. |
| 4,358,105 A | 11/1982 | Sweeney, Jr. |
| 4,361,154 A | 11/1982 | Pratt, Jr. |
| 4,365,359 A | 12/1982 | Raab |
| 4,383,533 A | 5/1983 | Bhagat et al. |
| 4,407,044 A | 10/1983 | Iseki |
| 4,410,158 A | 10/1983 | Maffei |
| 4,421,119 A | 12/1983 | Pratt, Jr. |
| 4,431,038 A | 2/1984 | Rome |
| 4,440,025 A | 4/1984 | Hayakawa et al. |
| 4,441,486 A | 4/1984 | Pounds |
| 4,446,586 A | 5/1984 | Reed et al. |
| 4,452,326 A | 6/1984 | Hanssen et al. |
| 4,467,659 A * | 8/1984 | Baumoel ................ 73/861.27 |
| 4,476,847 A | 10/1984 | Taenzer et al. |
| 4,482,942 A | 11/1984 | Blaisdell et al. |
| 4,511,921 A | 4/1985 | Harlan et al. |
| 4,530,360 A | 7/1985 | Duarte |
| 4,536,894 A | 8/1985 | Galante et al. |
| 4,542,539 A | 9/1985 | Rowe, Jr. et al. |
| 4,542,744 A | 9/1985 | Barnes et al. |
| 4,550,714 A | 11/1985 | Talish |
| 4,556,066 A | 12/1985 | Semrow |
| 4,557,148 A * | 12/1985 | Akiyama ................ 73/861.28 |
| 4,570,487 A * | 2/1986 | Gruber ........................ 73/624 |
| 4,570,640 A | 2/1986 | Barsa |
| 4,570,927 A | 2/1986 | Petrofsky et al. |
| 4,573,996 A | 3/1986 | Kwiatek et al. |
| 4,594,662 A | 6/1986 | Devaney |
| 4,612,160 A | 9/1986 | Donlevy et al. |
| 4,627,429 A | 12/1986 | Tsuk |
| 4,630,323 A | 12/1986 | Sage et al. |
| 4,644,942 A | 2/1987 | Sump |
| 4,646,725 A | 3/1987 | Moasser |
| 4,657,543 A | 4/1987 | Langer et al. |
| 4,669,483 A | 6/1987 | Hepp et al. |
| 4,677,438 A | 6/1987 | Michiguchi et al. |
| 4,680,967 A * | 7/1987 | Rost ............................. 73/628 |
| 4,687,195 A | 8/1987 | Potts |
| 4,689,986 A | 9/1987 | Carson et al. |
| 4,708,127 A | 11/1987 | Abdelghani |
| 4,710,655 A | 12/1987 | Masaki |
| 4,725,272 A | 2/1988 | Gale |
| 4,726,099 A | 2/1988 | Card |
| 4,763,661 A | 8/1988 | Sommer et al. |
| 4,770,184 A | 9/1988 | Greene, Jr. et al. |
| 4,774,959 A | 10/1988 | Palmer et al. |
| RE32,782 E | 11/1988 | Pratt, Jr. |
| 4,782,822 A | 11/1988 | Ricken |
| 4,787,070 A | 11/1988 | Suzuki et al. |
| 4,787,888 A | 11/1988 | Fox |
| 4,792,336 A | 12/1988 | Hlavacek et al. |
| 4,802,477 A | 2/1989 | Gabbay |
| 4,830,015 A | 5/1989 | Okazaki |
| 4,836,316 A | 6/1989 | Carnevale et al. |
| 4,855,911 A | 8/1989 | Lele et al. |
| 4,858,599 A | 8/1989 | Halpern |
| 4,867,169 A | 9/1989 | Machida et al. |
| 4,891,849 A | 1/1990 | Robinson |
| 4,905,671 A | 3/1990 | Senge et al. |
| 4,913,157 A | 4/1990 | Pratt, Jr. et al. |
| 4,917,092 A | 4/1990 | Todd et al. |
| 4,917,376 A | 4/1990 | Lo |
| 4,920,966 A | 5/1990 | Hon et al. |
| 4,926,870 A | 5/1990 | Brandenburger |
| 4,928,959 A | 5/1990 | Bassett et al. |
| 4,930,358 A * | 6/1990 | Motegi et al. ............ 73/861.28 |
| 4,932,951 A | 6/1990 | Liboff et al. |
| 4,933,230 A | 6/1990 | Card et al. |
| 4,936,303 A | 6/1990 | Detwiler et al. |
| 4,941,474 A | 7/1990 | Pratt, Jr. |
| 4,947,853 A | 8/1990 | Hon |
| 4,979,501 A | 12/1990 | Valchanov et al. |
| 4,982,730 A | 1/1991 | Lewis, Jr. |
| 4,984,462 A | 1/1991 | Hass, Jr. et al. |
| 4,986,275 A | 1/1991 | Ishida et al. |
| 4,993,413 A | 2/1991 | McLeod et al. |
| 4,995,883 A | 2/1991 | Demane et al. |
| 5,000,183 A | 3/1991 | Bonnefous |
| 5,000,442 A | 3/1991 | Dalebout et al. |
| 5,003,965 A | 4/1991 | Talish et al. |
| 5,004,476 A | 4/1991 | Cook |
| 5,016,641 A | 5/1991 | Schwartz |
| 5,018,285 A | 5/1991 | Zolman et al. |
| 5,046,484 A | 9/1991 | Bassett et al. |
| 5,054,490 A | 10/1991 | Rossman et al. |
| 5,067,940 A | 11/1991 | Liboff et al. |
| 5,080,672 A | 1/1992 | Bellis |
| 5,088,976 A | 2/1992 | Liboff et al. |
| 5,099,702 A | 3/1992 | French |
| 5,100,373 A | 3/1992 | Liboff et al. |
| 5,103,806 A | 4/1992 | McLeod et al. |
| 5,106,361 A | 4/1992 | Liboff et al. |
| 5,107,853 A | 4/1992 | Plyter |
| 5,108,452 A | 4/1992 | Fallin |
| 5,133,420 A | 7/1992 | Smith |
| 5,134,999 A | 8/1992 | Osipov |
| 5,139,498 A | 8/1992 | Astudillo Ley |
| 5,140,988 A | 8/1992 | Stouffer et al. |
| 5,143,069 A | 9/1992 | Kwon et al. |
| 5,143,073 A | 9/1992 | Dory |
| 5,154,189 A | 10/1992 | Oberlander |
| 5,163,598 A | 11/1992 | Peters et al. |
| 5,172,692 A | 12/1992 | Kulow et al. |
| 5,178,134 A | 1/1993 | Vago |
| 5,181,512 A | 1/1993 | Viebach et al. |
| 5,184,605 A | 2/1993 | Grzeszykowski |
| 5,186,162 A | 2/1993 | Talish et al. |
| 5,191,880 A | 3/1993 | McLeod et al. |
| 5,197,475 A | 3/1993 | Antich et al. |
| 5,201,766 A | 4/1993 | Georgette |
| 5,209,221 A | 5/1993 | Riedlinger |

| | | |
|---|---|---|
| 5,211,160 A | 5/1993 | Talish et al. |
| 5,230,334 A | 7/1993 | Klopotek |
| 5,230,345 A | 7/1993 | Curran et al. |
| 5,230,646 A | 7/1993 | Thorup |
| 5,230,921 A | 7/1993 | Waltonen et al. |
| 5,235,981 A | 8/1993 | Hascoet et al. |
| 5,254,123 A | 10/1993 | Bushéy |
| 5,259,384 A | 11/1993 | Kaufman et al. |
| 5,269,306 A | 12/1993 | Warnking et al. |
| 5,273,028 A | 12/1993 | McLeod et al. |
| 5,280,728 A * | 1/1994 | Sato et al. ............... 73/861.28 |
| 5,284,143 A | 2/1994 | Rattner |
| 5,285,788 A | 2/1994 | Arenson et al. |
| 5,295,931 A | 3/1994 | Dreibelbis et al. |
| 5,301,683 A | 4/1994 | Durkan |
| 5,307,284 A | 4/1994 | Brunfeldt et al. |
| 5,309,898 A | 5/1994 | Kaufman et al. |
| 5,310,408 A | 5/1994 | Schryver et al. |
| 5,314,401 A | 5/1994 | Tepper |
| 5,316,000 A | 5/1994 | Chapelon et al. |
| 5,318,561 A | 6/1994 | McLeod et al. |
| 5,318,779 A | 6/1994 | Hakamatsuka et al. |
| 5,322,067 A | 6/1994 | Prater et al. |
| 5,323,769 A | 6/1994 | Bommannan et al. |
| 5,327,890 A | 7/1994 | Matura et al. |
| 5,330,481 A | 7/1994 | Hood et al. |
| 5,330,489 A | 7/1994 | Green et al. |
| 5,334,214 A | 8/1994 | Putnam |
| 5,339,804 A | 8/1994 | Kemp |
| 5,340,510 A | 8/1994 | Bowen |
| 5,351,389 A | 10/1994 | Erickson et al. |
| 5,363,850 A | 11/1994 | Soni et al. |
| 5,366,465 A | 11/1994 | Mirza |
| 5,367,500 A | 11/1994 | Ng |
| 5,368,044 A | 11/1994 | Cain et al. |
| 5,376,065 A | 12/1994 | McLeod et al. |
| 5,380,269 A | 1/1995 | Urso |
| 5,386,830 A | 2/1995 | Powers et al. |
| 5,393,296 A | 2/1995 | Rattner |
| 5,394,877 A | 3/1995 | Orr et al. |
| 5,394,878 A | 3/1995 | Frazin et al. |
| 5,398,290 A | 3/1995 | Brethour |
| 5,400,795 A | 3/1995 | Murphy et al. |
| 5,405,389 A | 4/1995 | Conta et al. |
| 5,409,446 A | 4/1995 | Rattner |
| RE34,959 E | 5/1995 | Potts |
| 5,413,550 A | 5/1995 | Castel |
| 5,415,167 A | 5/1995 | Wilk |
| 5,417,215 A | 5/1995 | Evans et al. |
| 5,424,550 A | 6/1995 | Kawano et al. |
| 5,425,954 A | 6/1995 | Thompson et al. |
| 5,431,612 A | 7/1995 | Holden |
| 5,434,827 A | 7/1995 | Bolorforosh |
| 5,441,051 A | 8/1995 | Hileman et al. |
| 5,441,058 A | 8/1995 | Fareed |
| 5,448,994 A | 9/1995 | Iinuma |
| 5,460,595 A | 10/1995 | Hall et al. |
| 5,466,215 A | 11/1995 | Lair et al. |
| 5,468,220 A | 11/1995 | Sucher |
| 5,476,438 A | 12/1995 | Edrich et al. |
| 5,478,306 A | 12/1995 | Stoner |
| 5,484,388 A | 1/1996 | Bassett et al. |
| 5,492,525 A | 2/1996 | Gibney |
| 5,495,846 A | 3/1996 | Uehara et al. |
| 5,496,256 A | 3/1996 | Bock et al. |
| 5,501,657 A | 3/1996 | Feero |
| 5,507,800 A | 4/1996 | Strickland |
| 5,507,830 A | 4/1996 | DeMane et al. |
| 5,509,933 A | 4/1996 | Davidson et al. |
| 5,520,612 A | 5/1996 | Winder et al. |
| 5,524,624 A | 6/1996 | Tepper et al. |
| 5,526,815 A | 6/1996 | Granz et al. |
| 5,541,489 A | 7/1996 | Dunstan |
| 5,547,459 A | 8/1996 | Kaufman et al. |
| 5,556,372 A | 9/1996 | Talish et al. |
| 5,578,060 A | 11/1996 | Pohl et al. |
| 5,615,466 A | 4/1997 | Safari et al. |
| 5,626,554 A | 5/1997 | Ryaby et al. |
| 5,626,630 A | 5/1997 | Markowitz et al. |
| 5,630,837 A | 5/1997 | Crowley |
| D380,440 S | 7/1997 | Talish et al. |
| 5,644,093 A | 7/1997 | Wright et al. |
| 5,648,941 A | 7/1997 | King |
| 5,656,016 A | 8/1997 | Ogden |
| 5,665,141 A | 9/1997 | Vago |
| 5,680,863 A | 10/1997 | Hossack et al. |
| 5,690,608 A | 11/1997 | Watanabe et al. |
| 5,691,960 A | 11/1997 | Gentilman et al. |
| 5,699,803 A | 12/1997 | Carodiskey |
| 5,702,353 A | 12/1997 | Guzzini et al. |
| 5,702,389 A | 12/1997 | Taylor et al. |
| 5,706,818 A | 1/1998 | Gondo |
| 5,708,236 A | 1/1998 | Shaanan et al. |
| 5,721,400 A | 2/1998 | Haraldsson et al. |
| 5,725,482 A | 3/1998 | Bishop |
| 5,728,095 A | 3/1998 | Taylor et al. |
| 5,730,705 A | 3/1998 | Talish et al. |
| 5,738,625 A | 4/1998 | Gluck |
| 5,741,317 A | 4/1998 | Ostrow |
| 5,743,862 A | 4/1998 | Izumi |
| 5,752,924 A | 5/1998 | Kaufman et al. |
| 5,755,746 A | 5/1998 | Lifshey et al. |
| 5,762,616 A | 6/1998 | Talish |
| 5,779,600 A | 7/1998 | Pape |
| 5,785,656 A | 7/1998 | Chiabrera et al. |
| 5,818,149 A | 10/1998 | Safari et al. |
| 5,829,437 A | 11/1998 | Bridges |
| 5,843,741 A | 12/1998 | Wong et al. |
| 5,856,622 A * | 1/1999 | Yamamoto et al. ........ 73/861.28 |
| 5,868,649 A | 2/1999 | Erickson et al. |
| 5,871,446 A | 2/1999 | Wilk |
| 5,886,302 A | 3/1999 | Germanton et al. |
| 5,891,143 A | 4/1999 | Taylor et al. |
| 5,899,425 A | 5/1999 | Corey Jr. et al. |
| 5,904,659 A | 5/1999 | Duarte et al. |
| 5,906,580 A | 5/1999 | Kline-Schoder et al. |
| 5,954,675 A | 9/1999 | Dellagatta |
| 5,957,814 A | 9/1999 | Eschenbach |
| 5,962,790 A | 10/1999 | Lynnworth et al. |
| 5,971,984 A | 10/1999 | Taylor et al. |
| 5,997,490 A | 12/1999 | McLeod et al. |
| 6,019,710 A | 2/2000 | Dalebout et al. |
| 6,022,349 A | 2/2000 | McLeod et al. |
| 6,028,066 A | 2/2000 | Unger |
| 6,030,386 A | 2/2000 | Taylor et al. |
| 6,048,323 A | 4/2000 | Hon |
| 6,050,943 A | 4/2000 | Slayton et al. |
| 6,061,597 A | 5/2000 | Rieman et al. |
| 6,065,350 A * | 5/2000 | Hill et al. ................. 73/861.27 |
| 6,068,596 A | 5/2000 | Weth et al. |
| 6,080,088 A | 6/2000 | Petersen et al. |
| 6,082,181 A * | 7/2000 | Greenwood ................ 73/32 A |
| 6,086,078 A | 7/2000 | Ferez |
| 6,088,613 A | 7/2000 | Unger |
| 6,093,135 A | 7/2000 | Huang |
| 6,105,431 A * | 8/2000 | Duffill et al. .................. 73/624 |
| 6,165,144 A | 12/2000 | Talish et al. |
| 6,179,797 B1 | 1/2001 | Brotz |
| 6,190,336 B1 | 2/2001 | Duarte et al. |
| 6,206,843 B1 | 3/2001 | Iger et al. |
| 6,213,958 B1 | 4/2001 | Winder |
| 6,234,975 B1 | 5/2001 | McLeod et al. |
| 6,234,990 B1 | 5/2001 | Rowe et al. |
| 6,258,020 B1 | 7/2001 | Lopez |
| 6,261,221 B1 | 7/2001 | Tepper et al. |
| 6,261,249 B1 | 7/2001 | Talish et al. |

| | | | |
|---|---|---|---|
| 6,264,650 B1 | 7/2001 | Hovda et al. | |
| 6,273,864 B1 | 8/2001 | Duarte et al. | |
| 6,311,402 B1 | 11/2001 | Brandl et al. | |
| 6,322,527 B1 | 11/2001 | Talish | |
| 6,355,006 B1 | 3/2002 | Ryaby et al. | |
| 6,360,027 B1 | 3/2002 | Hossack et al. | |
| 6,394,955 B1 | 5/2002 | Perlitz | |
| 6,397,683 B1 | 6/2002 | Hagenmeyer et al. | |
| 6,406,443 B1 | 6/2002 | Talish | |
| 6,436,060 B1 | 8/2002 | Talish | |
| 6,443,898 B1 | 9/2002 | Unger | |
| 6,464,687 B1 | 10/2002 | Ishikawa et al. | |
| 6,503,214 B1 | 1/2003 | Talish | |
| 6,524,261 B2 | 2/2003 | Talish et al. | |
| 6,685,656 B1 | 2/2004 | Duarte et al. | |
| 6,733,468 B2 | 5/2004 | Talish | |
| 6,932,308 B2 | 8/2005 | Talish et al. | |
| 6,960,173 B2 | 11/2005 | Babaev | |
| 7,108,663 B2 | 9/2006 | Talish | |
| 7,211,060 B1 | 5/2007 | Talish | |
| 2002/0016557 A1 | 2/2002 | Duarte | |
| 2002/0068871 A1 | 6/2002 | Mendlein et al. | |
| 2002/0103448 A1 | 8/2002 | Babaev | |
| 2002/0115960 A1 | 8/2002 | Redding, Jr. | |
| 2002/0156400 A1 | 10/2002 | Babaev | |
| 2002/0190136 A1 | 12/2002 | Babaev | |
| 2003/0013956 A1 | 1/2003 | Michaeli | |
| 2003/0153848 A1 | 8/2003 | Talish | |
| 2003/0153849 A1 | 8/2003 | Huckle | |
| 2004/0127790 A1 | 7/2004 | Lang et al. | |
| 2005/0096548 A1 | 5/2005 | Talish | |
| 2006/0106424 A1 | 5/2006 | Bachem | |

FOREIGN PATENT DOCUMENTS

| | | |
|---|---|---|
| CA | 1328485 | 4/1994 |
| DE | 3639263 A1 | 6/1987 |
| DE | 4111055 A1 | 10/1991 |
| DE | 19613425 | 1/1997 |
| DE | 29811185 U1 | 10/1998 |
| EP | 0 181 506 A2 | 5/1986 |
| EP | 331 348 A1 | 9/1989 |
| EP | 0425765 A1 * | 5/1991 |
| EP | 0 536 875 A1 | 4/1993 |
| EP | 0 679 371 A1 | 11/1995 |
| EP | 0 695 559 | 2/1996 |
| EP | 0 965 839 A1 | 12/1999 |
| GB | 2156983 A | 10/1985 |
| GB | 2277448 A | 11/1994 |
| GB | 2 303 552 A | 2/1997 |
| JP | SHO 62-47359 | 3/1987 |
| JP | HEI 4 1992-82567 | 3/1992 |
| JP | HEI 4-82567 | 3/1992 |
| JP | HEI 4-82568 | 3/1992 |
| JP | HEI 4-82569 | 3/1992 |
| JP | HEI 5-269159 | 10/1993 |
| WO | WO 85/03449 | 8/1985 |
| WO | WO 88/00845 | 2/1988 |
| WO | WO 88/02250 | 4/1988 |
| WO | WO 90/06720 | 6/1990 |
| WO | WO 94/13411 | 6/1994 |
| WO | WO 95/03744 | 2/1995 |
| WO | WO 95/33416 | 12/1995 |
| WO | WO 96/25112 | 8/1996 |
| WO | WO 96/25888 | 8/1996 |
| WO | WO 97/33649 | 9/1997 |
| WO | WO 98/10729 | 3/1998 |
| WO | WO 98/29036 | 7/1998 |
| WO | WO 98/34578 | 8/1998 |
| WO | WO 98/47570 | 10/1998 |
| WO | WO 99/18876 | 4/1999 |
| WO | WO 99/22652 | 5/1999 |
| WO | WO 99/48621 | 9/1999 |
| WO | WO 99/56829 | 11/1999 |
| WO | WO 99/58080 | 11/1999 |
| WO | WO 00/03663 | 1/2000 |
| WO | WO 00/28925 | 5/2000 |
| WO | WO 00/67846 | 11/2000 |
| WO | WO 00/71207 | 11/2000 |
| WO | WO 00/76406 | 12/2000 |

OTHER PUBLICATIONS

Photographs of Exercise Ergometer Developed by Biodex Medical Systems, Shirley, New York (3 pages, 2002).
"Generation of Electric Potentials by Bone in Response to Mechanical Stress," *Science Magazine*, 137, 1063-1064 (Sep. 28, 2002).
Caplan, et al., *Clinical Orthopaedics and Related Research*, No. 342:254-269 (1997).
Moran, et al., *The Journal of Bone and Joint Surgery*, 74-B:659-667 (1992).
Cass, "Fabrication of Continuous Ceramic Fiber by the Viscous Suspension Spinning Process," *Ceramic Bulletin*, vol. 70, No. 3, pp. 424-429 (1991).
Clarke, P.R. et al., "Physical and Chemical Aspects of Ultrasonic Disruption of Cells", *JASA* (1969), 47(2): 649-653.
Hill, C.R., "Ultrasonic Exposure Thresholds for Changes in Cells and Tissues", *JASA* (1972), 52(2): 667-672.
McLeod, et al., "Improved Postural Stability Following Short Term Exposure to Low Level Whole Body Vibration," 44th Annual Meeting, Orthopaedic Research Society, Mar. 16-19, 1998, New Orleans, Louisiana, p. 89-15.
Phoenix (Business Wire), Jul. 8, 1997 via CompanyLink—OrthoLogic Corp.
Pilgrim, et al., "An Extension of the Composite Nomenclature Scheme," Med. Res. Bull., vol. 22, pp. 877-894 (1987).
"Reflex Sympathetic Dystrophy, Does RSD Exist?" www.arbon.com (Jun. 4, 1997).
"Reflex Sympathetic Dystrophy: The Pain That Doesn't Stop," tcc.cc.nc.us (Jun. 4, 1997).
RSDnet.org "Reflex Sympathetic Dystrophy," www.rsdnet.org (Jun. 4, 1997).
Tavakoli and Evans , "The Effect of Bone Structure on Ultrasonic Attenuation and Velocity," *Ultrasonics*, vol. 30, No. 6 (1992).
Patent Abstracts vol. 13, n. 541 (E-854), Dec. 5, 1989, Japan.
ABSTRACT, (Proceedings of the 11th Int'l. Conference on Medical and Biological Engineering) "Ultrasonic Stimulation of Fracture Healing", 1976.
ABSTRACT, (Proceedings of the III Congress on Biomedical Engineering) "Ultrasonic Action on Callus Formation in Bones", 1975.
ABSTRACT, (Proceedings of the IV Brazilain Congress on Biomedical Engineering) "Ultrasound in the Treatment of Fractures", 1977.
ASTM Designation: D790M-93 Metric, "Standard Test Methods for flexural Properties of Unreinforced and Reinforced Plastics and Electrical Insluating Materials (Metric)", pp. 176-184, (Dec. 1993).
ASTM Designation: C1161-90, "Standard Test Method for Flexural Strength of Advanced Ceramics at Ambient Temperature," pp. 324-330.(Feb. 1991).
Brochure: "The Science Behind the Technology," distributed by Smith & Nephew for EXOGEN, no date.
Arai et al., "The Effect of Ultrasound Stimulation on Disuse Osteoporosis", Brags 17, 1993.
Berridge, M.J., "Inositol Trisphosphate and Calcium Signaling", *Nature* (1993), 361: 315-325.
Clarke, P.R. et al., "Physical and Chemical Aspects of Ultrasonic Disruption of Cells", *JASA* (1969), 47(2): 649-653.
Duarte, L.R., "The Stimulation of Bone Growth by Ultrasound", *Arch. Orthop. Trauma Surg* (1983), 101: 153-159.
Dyson, M., "Therapeutic Applications of Ultrasound", *Biological Effects of Ultrasound* (1985), Nyborg, W.L. and Ziskin, M.C., eds; Churchill Livingstone Inc., New York, Chapter 11.
Goodship, A.E. et al., "The Influence of Induced Micromovement Upon the Healing of Experimental Tibial Fractures", *J. Bone and Joint Surg.* (1985), 67-B(4): 650-655.

Heckman, J.D. et al., "Acceleration of Tibial Fracture Healing by Non-Invasive Low-Intensity Pulsed Ultrasound", *J. Bone and Joint Surg.* (1994), 76-A(1): 26-34.

Hill, C.R., "Ultrasonic Exposure Thresholds for Changes in Cells and Tissues", *JASA* (1972), 52(2): 667-672.

Howkins, S.D., "Diffusion Rates and the Effect of Ultrasound", *Ultrasonics* (1969), 129-130.

Kristiansen, T.K. et al., "Accerlated Healing of Distal Radial Fractures with the Use of Specific, Low-Intensity Ultrasound", *J. Bone and Joint Surg.* (1997), 79-A(7) 961-973.

Maurice Hilario, "Low-Intensity Ultrasound Radiation in the Tissue Repair of Trophic Leg Ulcers", 1983, University of Sao Paulo, pp. 1-125.

Pethica, B.A., et al., Abstract, Biological Repair and Growth Society, Jun. 1998.

Phoenix (Business Wire), Jul. 8, 1997 via CompanyLink—OrthoLogic Corp.

Pilla, A.A. et al., "Non-Invasive Low-Intensity Ultrasound Accelerates Bone Repair: Rabbit Fiubla Model and Human Colles' and Tibial Fractures", *Annual Intl. Conference of IEEE-EMBS Proceedings* (1990), 12:1573-1574.

Ter Haar, G., et al., "Basic Physics of Therapeutic Ultrasound", *Physiotherapy* (1987), 73(3): 110-113.

Wallace, A.L.; Draper E.R.C.; Strachan, R.K.; McCarthy, I.D.; Hughes, S.P.F., "The Vascular Response to Fracture Micromovement", *Clinical Orthopaedics and Related Research* (1994), 301: 281-290.

Wang, S.J. et al., "Low-Intensity Ultrasound Treatment Increases Strength in a Rat Femoral Fracture Model", *J. Ortho Research* (1994), 12: 40-47.

Webster, D.F.et al., "The Role of Ultrasound-Induced Cavitation in the 'In Vitro' Stimulation of Collagen Synthesis in Human Fibroblasts", *Ultrasonics* (1980), 33-37.

Yang, K.H. et al., "Exposure to Low-Intensity Ultrasound Treatment Increases Aggrecan Gene Expression in a Rat Femur Fracture Model", *J. Ortho Research* (1996), 14:802-809.

Treatment of Osteochondral Defects in Rabbits with SAFHS—Parts I and II, EX1095-01R, EX1096-01R, no date.

Treatment of Osteochondral Defects in Rabbits with SAFHS—Part III, EX 1097-01R (Aug. 26, 1997).

Cook, Stephen and L. Patron, "Treatment of Osteorchondral Defects in Rabbits with SAFHS—A Mosalcplasty Model"—Final Report, EX1098-04R (Aug. 12, 1999).

Acoustic Emission—An Update, by Arthur E. Lord, Jr., 1981, Physical Acoustics, vol. XV, pp. 295-360.

Acoustic Emission and Diagnosis of Osteoporosis, by S. Hanagud, G. T. Hannon and R. Clinton, 1974, Ultrasonic Symposium Proceedings (IEEE), pp. 77-81.

Acoustic Emission in Bone Substance, by S. Hanagud, R.G. Clinton and J.P. Lopez, 1973, Biomechanics Symposium Proceedings (ASME), pp. 79-81.

Acoustic Emission Inspection, by Adrian A. Pollock, 1992, ASM Handbook, vol. 17, Nondestructive Evaluation and Quality Control, pp. 278-293.

Acoustic Emission Techniques in the Development of a Diagnostic Tool for Osteoporosis, by S. Hanagud and R. G. Clinton, 1975, Ultrasonic Symposium Proceedings (IEEE), pp. 41-45.

Application of an intelligent signal processing system to acoustic emission analysis, by Igo Grabec and Wolfgang Sachse, Mar. 1989, Acoustic Society of America, pp. 787-791.

Application of correlation techniques for localization of acoustic emission sources, by I. Grabec, 1978, IPC Business Press Ltd., pp. 111-115.

Cornejo, et al., "Large-Area Flexible-Array Piezoelectric Ceramic/Polymer composite Transducer for Bone Healing Acceleration," presented at ISAFXI, Montreux, Switzerland (1998).

Clough, R. and J. Simmons, "Theory of Acoustic Emission," Metallurgy Division, national Bureua of Standards, no date.

Fritton, et al., "Whole-Body Vibration in the Skeleton: Development of a Resonance-Based Testing Device," *Annals of Biomedical Engineering*, vol. 25, pp. 831-839 (1997).

Goodship, et al., "Low magnitude high frequency mechanical stimulation of endochondral bone repair" 43rd Annual Meeting Orthopeadic Research Society, vol. 22, Sec. 1, Feb. 9-13, 1997.

J. Kenwright, et al., "Controlled Mechanical Stimulation in the Treatment of Fibial Fractures," Orthopedics, Clinical Orthopedics and Related Research (1989) 241:36-47.

Jankovich, "The Effects of Mechanical Vibration on Bone Development in the Rat," *J. Biomechanics*, 1972, vol. 5, pp. 241-250.

Ko, Preform Fiber Architecture for Ceramic-Matrix Composites, Ceramic Bulletin, vol. 68, No. 2, pp. 401-414(1989).

McLeod, et al., "Improved Postural Stability Following Short Term Exposure to Low Level Whole Body Vibration," 44th Annual Meeting, Orthopaedic Research Society, Mar. 16-19, 1998, New Orleans, Louisiana, p. 89-15.

Newnham, et al., Connectivity and Piezoelectric-Pyroelectric Composites, Med. Res. Bull., vol. 13, pp. 525-536 (1978).

Pauer, "Flexible Piezoelectric Material," pp. 1-5, no date.

Pilgrim, et al., "An Extension of the Composite Nomenclature Scheme," Med. Res. Bull., vol. 22, pp. 877-894 (1987).

Powell, et al., "A Performance Appraisal of Flexible Array Structures Using a Facet Ensemble Scattering Technique," *1991 Ultrasonic Symposium*, pp. 753-766.

Powell, et al., Flexible Ultrasonic Transducer Arrays for Nondestructive Evaluation Applications—Part 1: The Theoretical Modeling Approach, *"IEEE Transactions on Ultrasonics, Ferroelectrics, and Frequency Control,"* vol. 43, No. 3, May 1996, pp. 385-392.

Powell, et al., "Flexible Ultrasonic Transducer Arrays for Nondestructive Evaluation Applications—Part II: Performance Assessment of different Array Configurations, *IEEE Transactions on Ultrasonics, Ferroelectrics, and Frequency Control,"* vol. 43, No. 3, May 1996, pp. 393-402.

Pethica, B.A., et al., Abstract, Biological Repair and Growth Society, Jun. 1998.

Goodship, et al., "Low magnitude high frequency mechanical stimulation of endochondral bone repair" 43rd Annual Meeting Orthopeadic Research Society, vol. 22, Sec. 1, Feb. 9-13, 1997.

Y. Qin, et al., "Correlation of In Vivo Bone Adaptation and Mechanical Parameters Using Low Magnitude, High Frequency Loading," 41st Annual Meeting Orthopaedic Research Soc., vol. 20—Sec. 1, Feb. 13-16, 1955.

Grewe, et al., "Acoustic Properties of Particle Polymer Composite for Ultrasonic Transducer Backing Applications," *IEEE*, (1990).

Wu and Cubberly, "Measurement if Velocity and Attenuation of Shear Waves in Bovine Compact Bone Using Ultrasonic Spectroscopy," Med. & Biol., vol. 23, No. 1,129-134, 1997.

Pilla, et al., "Non-Invasive Low-Intensity Pulsed Ultrasound Accelerates Bone Healing in the Rabbit," *Journal of Orthopaedic Trauma*, vol. 4, No. 3, pp. 246-253 (1990).

Bascom, "Other Continuous Fibers," 118/Constitutent Material Form, no date.

Bascom, "Other Discontinuous Forms," 120/Constituent Materials Forms, no date.

Niemczewaki, B., "A Comparison of Ultrasonic Cavitation Intensity in Liquids," *Ultrasonics*, May 1980, pp. 107-110.

Sarvazyan, "Some General Problems of Biological Action of Ultrasound," IEEE Transactions on Sonics and Ultrasonics, vol. 30, No. 1, Jan. 1983.

Ultrasound as a Tool for Investigating Bone: Fundamental Principles and Perspectives for Use in Osteoporosis, by J. G. Bioch, 1993, Expanson Scientifique Francaise.

Y. Qin, et al., "Correlation of In Vivo Bone Adaptation and Mechanical Parameters Using Low Magnitude, High Frequency Loading," 41st Annual Meeting Orthopaedic Research Soc., vol. 20—Sec. 1, Feb. 13-16, 1955.

Bascom, "Other Continuous Fibers," 118/Constitutent Material Form, no date.

Bascom, "Other Discontinuous Forms," 120/Constituent Materials Forms, no date.

Cass, "Fabrication of Continuous Ceramic Fiber by the Viscous Suspension Spinning Process," *Ceramic Bulletin*, vol. 70, No. 3, pp. 424-429 (1991).

"Development of Flexible Pieoelectric Transducers and Matching Layers for EXOGEN Incorporated," Final Report, Covering Period Apr. 1, 1997 to Feb. 28, 1998, Rutgers University.

Grewe, et al., "Acoustic Properties of Particle Polymer Composite for Ultrasonic Transducer Backing Applications," *IEEE*, (1990).

Grewe, Martha G., "Acoustic Matching And Backing Layer for Medical Ultrasonic Transducers," A Thesis in Solid State Science, The Pennsylvania State University; (May 1989), The Center for Ceramics Research, Rutgers.

Gururaja, T., "Piezoelectric Composite Materials for Ultrasonic Transducer Applications," A Thesis in Solid State Science, The Pennsylvania State University, May 1984.

Gururaja, "Piezoelectrics for Medical Ultrasonic Imaging," *Am. Ceram. Soc. Bull.*, vol. 73, No. 5, pp. 50-55 (May 1994).

Hall, et al., "The design and evaluation of ultrasonic arrays using 1-3 connectivity composites," *SPIE*, pp. 216-227, vol. 1733 (1992).

Pilla, et al., "Non-Invasive Low-Intensity Pulsed Ultrasound Accelerates Bone Healing in the Rabbit," *Journal of Orthopaedic Trauma*, vol. 4, No. 3, pp. 246-253 (1990).

Safari, "Development of piezoelectric composites for transducers," *J. Phys.France*, 4:1129-1149 (1994).

Selfridge, "Approximate Material Properties in Isotropic Materials," *IEEE Transactions on Sonics and Ultrasonics*, May 9, 1985.

Souquet, et al., "Design of Low-Loss Wide-Band Ultrasonic Transducers for Noninvasive Medical Application," *IEEE Transactions on Sonics and Ultrasonics*, pp. 75-81, vol. SU-26, No. 2, Mar. 1979.

Waller, et al., "Poling of Lead Zirconate Titanate Ceramics and Flexible Piezoelectric Composites by the Corona Discharge Technique," *J. Am. Ceram. Soc.*, 72(2):322-24 (1989).

Winder, Alan, "Synthetic Structural Imaging and Volume Estimation of Biological Tissue Organs,", Acoustic Sciences Associates, Dec. 1995.

Winder, Alan, "Acoustic Emission Monitoring for the Detection, Localization and Classification of Metabolic Bone Disease," Acoustic Sciences Associates, Dec. 1995.

Wu and Cubberly, "Measurement of Velocity and Attenuation of Shear Waves in Bovine Compact Bone Using Ultrasonic Spectroscopy," Med. & Biol., vol. 23, No. 1,129-134, 1997.

Tavakoll and Evans , 1992 (no other information available at this time).

* cited by examiner

METHOD AND APPARATUS FOR CONTROLLING ACOUSTIC MODES IN TISSUE HEALING APPLICATIONS

FIELD OF THE INVENTION

This invention relates to therapeutic ultrasound devices, and more particularly, to the use of coupling systems to control the angles at which the acoustic waves are delivered from one or more transducers to the human body, thereby facilitating the transfer of acoustic energy into specific acoustic modes upon incidence of the acoustic waves at the skin tissue and bone tissue interfaces or surfaces, to further promote tissue healing for both shallow and deep anatomical structures.

BACKGROUND OF THE INVENTION

Ultrasound has been used as a therapeutic technique in physical medicine for over 45 years. It has been a recommended treatment technique for adjunctive therapy for the treatment of pain, soft tissue injury, and joint dysfunction including osteoarthritis, periarthritis, bursitis, tenosynovitis, and a variety of musculoskeletal syndromes. Additionally, ultrasound has been used in applications such as acceleration of wound healing, phonophoresis of topical drugs, treatment of scar tissue, and treatment of sports injuries.

The therapeutic biological effects of ultrasound may be characterized into two major areas: thermal and nonthermal. The nonthermal effects can include acoustic streaming, cavitation, and other mechanical effects over the broad range of ultrasonic frequencies from about 0.05 MHz (megahertz) to about 5.0 MHz. The electrical output from a signal generator is converted into mechanical vibration through a transducer which is generally made of a piezoelectric material, such as lead zirconate titanate (PZT), single-crystal ferroelectric relaxors, such as PMN-PZ-PT, or the like. The mechanical vibration produces an acoustic wave which travels through the tissue and is absorbed in the propagating process. The rate of viscous absorption and the associated increase in temperature are dependent on the micro-structural properties of the tissue-type encountered, the frequency of the acoustic wave, the spatial-temporal acoustic intensity and the degree of non-linear propagation in tissue. The acoustic energy may be in the form of a continuous wave or a pulsed wave, depending on the therapeutic application, and is typically transferred from the transducer to the patient's tissue using an acoustic coupling material, such as an ultrasonic gel, lotion, hydrogel, or water. Acoustic intensities of 0.03 to 3.0 W/cm² (Watts per square centimeter) are typically applied for therapeutic purposes, in pulsed or continuous modes, allowing treatment of bone fractures and acute, as well as chronic, tissue injury.

While the beneficial aspects of ultrasound have been explored, as evident in U.S. Pat. No. 4,530,360 to Duarte, U.S. Pat. No. 5,003,965 to Talish et al., U.S. Pat. No. 5,413,550 to Castel, and U.S. Pat. No. 5,520,612 to Winder et al., no device has been disclosed in the art to control the angle at which the acoustic waves are delivered to specific targeted tissue sites or to control the acoustic mode itself. Typically, therapeutic ultrasound treatment is administered by utilizing a piezoelectric transducer to generate acoustic longitudinal waves that propagate in tissue, primarily as longitudinal waves, to the treatment area. If the incident longitudinal waves are not normal to the piezoelectric transducer/skin tissue interface, the resulting refracted acoustic waves in the subsequent soft tissue propagate as quasi-longitudinal waves and quasi-shear waves at various refraction angles. As a result, it is often difficult to administer the acoustic waves to patients in the desired alignment with the targeted tissue area using the means for therapeutic ultrasound devices that are currently available. These devices cannot effectively control, explicitly or implicitly, the nature of the acoustic waves to the treatment area. Therefore, a need exists for an apparatus capable of facilitating control of the angle or angles at which acoustic longitudinal and shear waves are selectively delivered to the targeted tissue sites to facilitate the therapeutic process.

SUMMARY OF THE INVENTION

Set forth below is a brief summary of the invention which solves the foregoing problems and provides benefits and advantages in accordance with the purposes of the a present invention as embodied and broadly described herein.

This invention relates to devices, systems, and methods that facilitate control of the refracted and reflected ultrasonic waves in tissue from various designated reflection sites to further promote healing at specific treatment areas. One aspect of the invention relates to a modal converter whose geometrical configuration permits the positioning of a plurality of transducers at various angles. The modal converter may have a trapezoidal-shaped cross-section which may be asymmetrical and is composed of a solid material having the ability to channel and support the propagation of acoustic waves without introducing significant refraction, distortion or attenuation of the acoustic waves.

Figure 1:
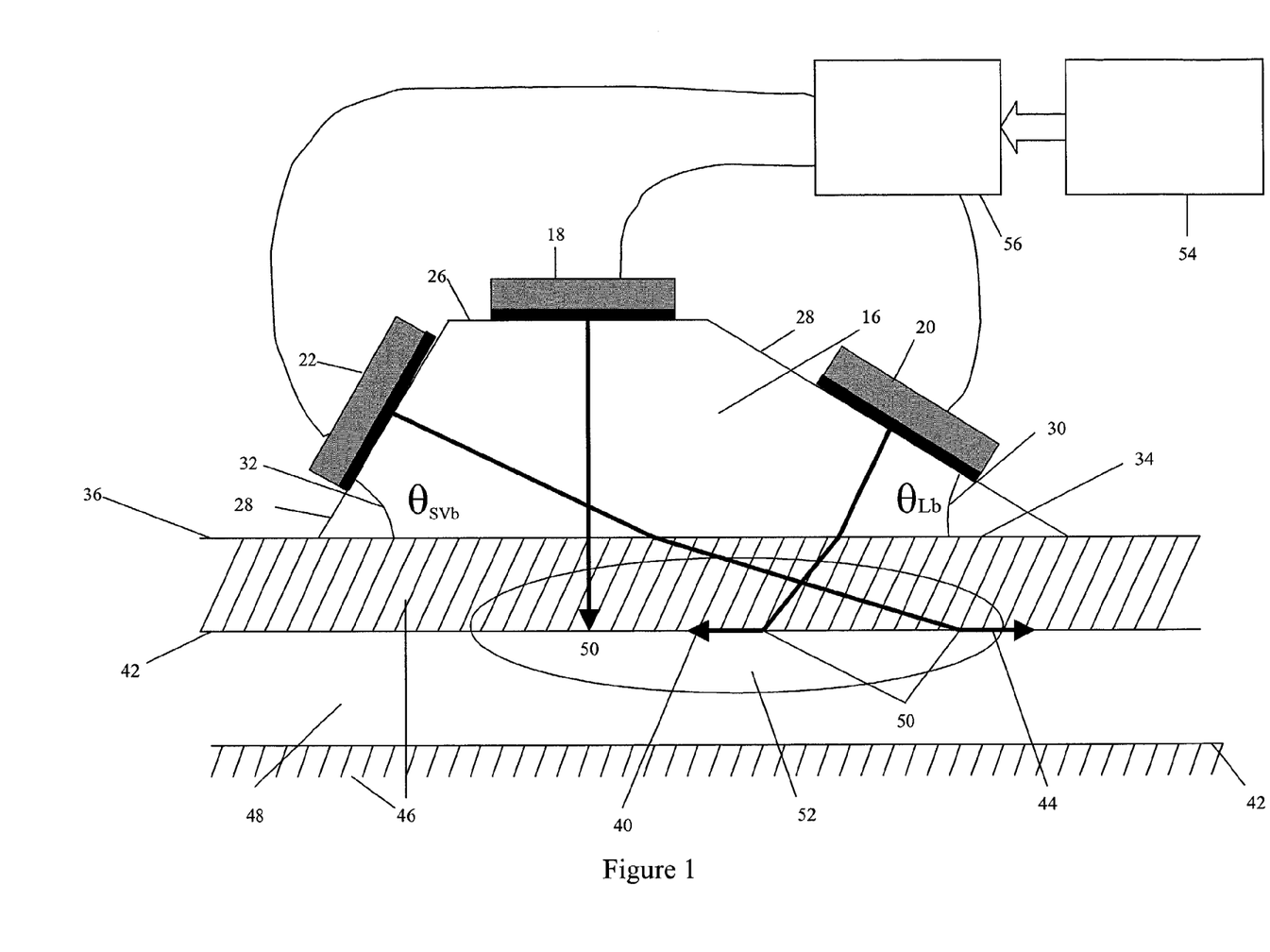
FIG. 1 is cross-sectional view of an embodiment of the modal converter configured as an asymmetrical trapezoidal wedge which depicts the first-critical angle ($\theta_{Lb}$) and the second-critical angle ($\theta_{SVb}$) for bone tissue.
Figure 2:
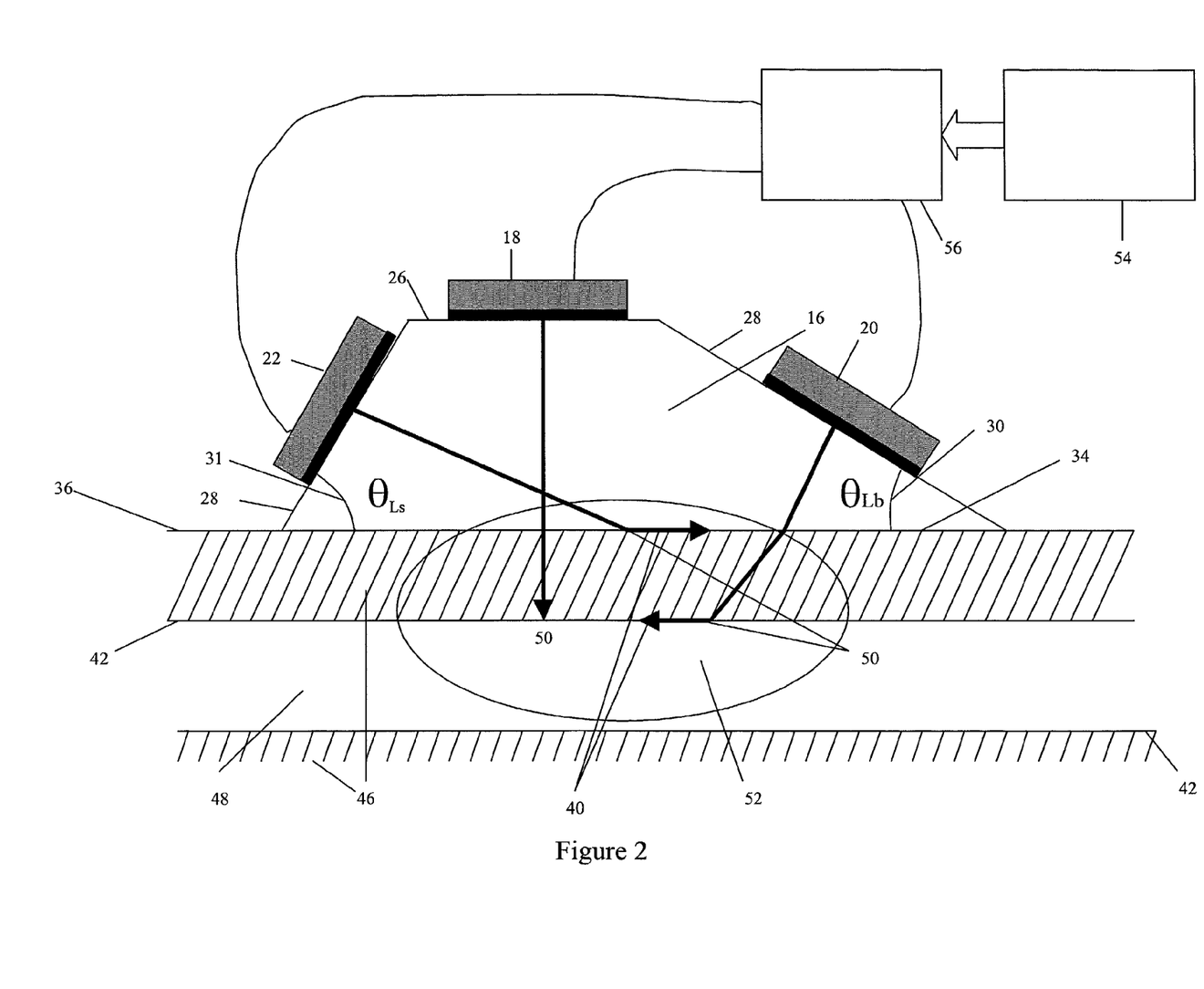
FIG. 2 is a cross-sectional view of an embodiment of the modal converter configured as an asymmetrical trapezoidal wedge which depicts the first-critical angle ($\theta_{Lb}$) for bone tissue and a steeper first-critical angle ($\theta_{Ls}$) for skin tissue.
Figure 3:
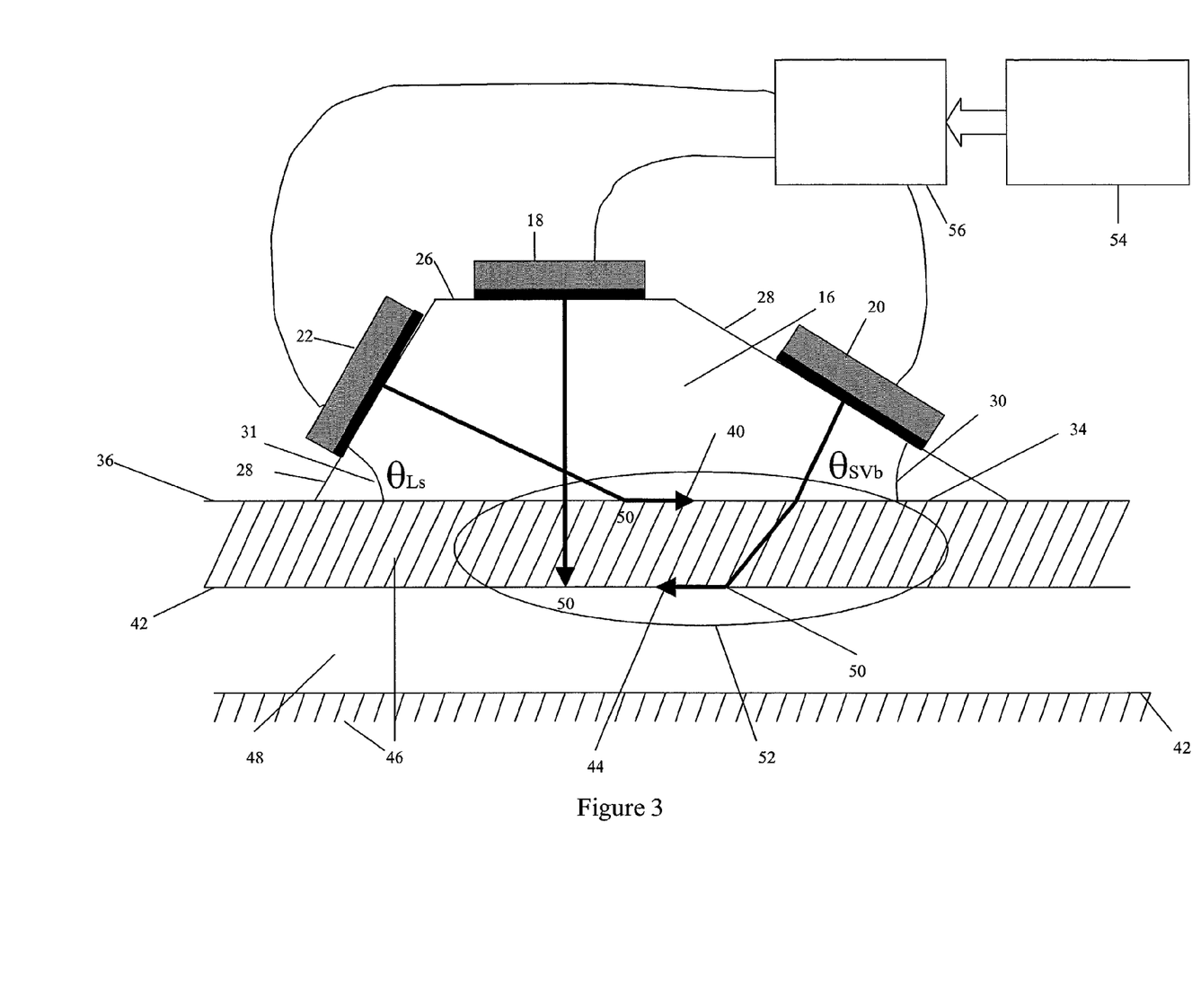
FIG. 3 is cross-sectional view of an alternative embodiment of the modal converter configured as an asymmetrical trapezoidal wedge which depicts the first-critical angle ($\theta_{Ls}$) for skin tissue and the second-critical angle ($\theta_{SVb}$) for bone tissue.

The modal converter provides distinct acoustic coupling paths through a plurality of transducers located in at least one of four ways. First, a transducer located on the top surface of the modal converter, with its transmitting face parallel to the skin tissue surface, transmits acoustic longitudinal waves perpendicular to the skin tissue and bone tissue surfaces. Second, a transducer located on an angled side of the modal converter at a first critical angle for bone tissue transmits acoustic longitudinal waves which strike the bone surface and are converted partially into longitudinal waves which travel parallel to the bone surface and partially into shear waves that travel at an angle determined by Poisson's ratio for bone tissue. Third, a transducer located on another angled side of the modal converter at a second critical angle for bone tissue transmits acoustic longitudinal waves which strike the bone surface and are totally converted into shear waves traveling parallel to the bone surface. Fourth, a transducer located on yet another angled side of the modal converter at a first critical angle for skin tissue transmits acoustic longitudinal waves which strike the skin tissue surface and are converted partially into longitudinal waves which travel parallel to the skin tissue surface and partially into shear waves that travel at an angle determined by Poisson's ratio for soft tissue. The modal converter device can incorporate and support any combination of these various coupling paths as depicted in FIGS. 1 through 3, and is an efficient means for converting longitudinal waves into shear waves for therapeutic applications.

In the following detailed description of this invention, the first medium may correspond with the modal converter or soft tissue, depending on the intervening interface being described. When the first medium corresponds to the modal converter, the second medium corresponds to soft tissue. In this instance, the first critical angle corresponds to an angle that produces a longitudinal mode component traveling along the skin tissue surface. When the first medium corresponds to soft tissue, the second medium corresponds to bone tissue. In this instance, the first critical angle corresponds to an angle that produces a longitudinal mode component traveling along the bone tissue surface, and the second critical angle corresponds to an angle that produces shear waves traveling along the bone tissue surface. Low intensity ultrasound longitudinal and shear waves are desired in order to increase the endostial and periostial phases of the bone fracture healing process.

Low intensity ultrasound has also been clinically demonstrated to enhance the process of angiogenesis or to increase blood flow around the bone fracture site, thereby further accelerating the healing of superficial musculo-skeletal tissue wounds and bone fractures. To facilitate control of the healing process, the transducers are controlled by a programmable micro-controller that permits sequential or simultaneous interrogation of the target tissue site with acoustic waves of different signal structure at various excitation rates.

BRIEF DESCRIPTION OF DRAWINGS

The accompanying drawings, which are incorporated in and form a part of the specification, illustrate embodiments of the present invention and, together with the description, disclose the principles of the invention. In the drawings:

FIGS. 1 through 3 illustrate only the refracted waves for the sake of drawing simplification, not the reflected longitudinal and shear waves produced by the oblique incidence of the longitudinal waves at the skin tissue and bone tissue surfaces.

DETAILED DESCRIPTION OF THE DRAWINGS

This present invention relates to a modal converter 16 which enables a user to control the angles at which acoustic longitudinal waves 40 and shear waves 44 are delivered to living tissue in order to effectuate a cascade of biological healing mechanisms. See FIG. 1. The modal converter 16 facilitates control of the spatial and temporal distribution of reflected energy from designated reflection sites 50 throughout the treatment area 52. The treatment area 52 may be composed of open tissue wounds or bone fractures, or both, with or without one or more surrounding musculoskeletal soft tissue wounds. Further, the surrounding soft tissue 46 may include, but is not limited to, tendons, muscles, ligaments, joints and bursae, peripheral nerves, skin, and subcutaneous fat. Control of both the absorbing and reflecting paths of acoustic waves in tissue can result in significant therapeutic benefits.

The modal converter 16 may have a trapezoidal cross-sectional shape, as shown in FIGS. 1 through 3 and 5. The modal converter 16 may also have other polygonal cross-sectional shapes which effectively locate the transducers at the desired angular orientation as set forth below in agreement with the spirit of this invention. Further, the following detailed description of the invention is provided for the purpose of explanation and is not intended to limit the presenting invention to the physical apparatus described herein. Instead, the invention includes any manner of interrogating a treatment area with ultrasonic acoustic waves in accordance with the invention set forth below.

The modal converter 16 may be composed of suitable low viscous loss materials which include, but are not limited to, thermoplastics, thermosets, elastomers and mixtures thereof. Useful thermoplastics include, but are not limited to, ethyl vinyl acetate, available from USI Corp (c/o Plastic Systems, Marlboro, Mass.), ecothane CPC 41, available from Emerson and Cumming (Deway and Almay Chemical division, Canton, Mass.), and polyurethane RP 6400, available from Ren Plastics (a Division of Ciba Geigy, Fountain Valley, Calif.). Useful thermosets include, but are not limited to, epoxies such as Spurr epoxy, available from Ernest F. Fullam, Inc. (Schenectady, N.Y.) and Stycast, available from Emerson and Cumming. Useful elastomers include, but are not limited to, RTV 60 and RTV 90, which are available from General Electric (Silicon Products Division, Waterford, N.Y.).

Figure 5:
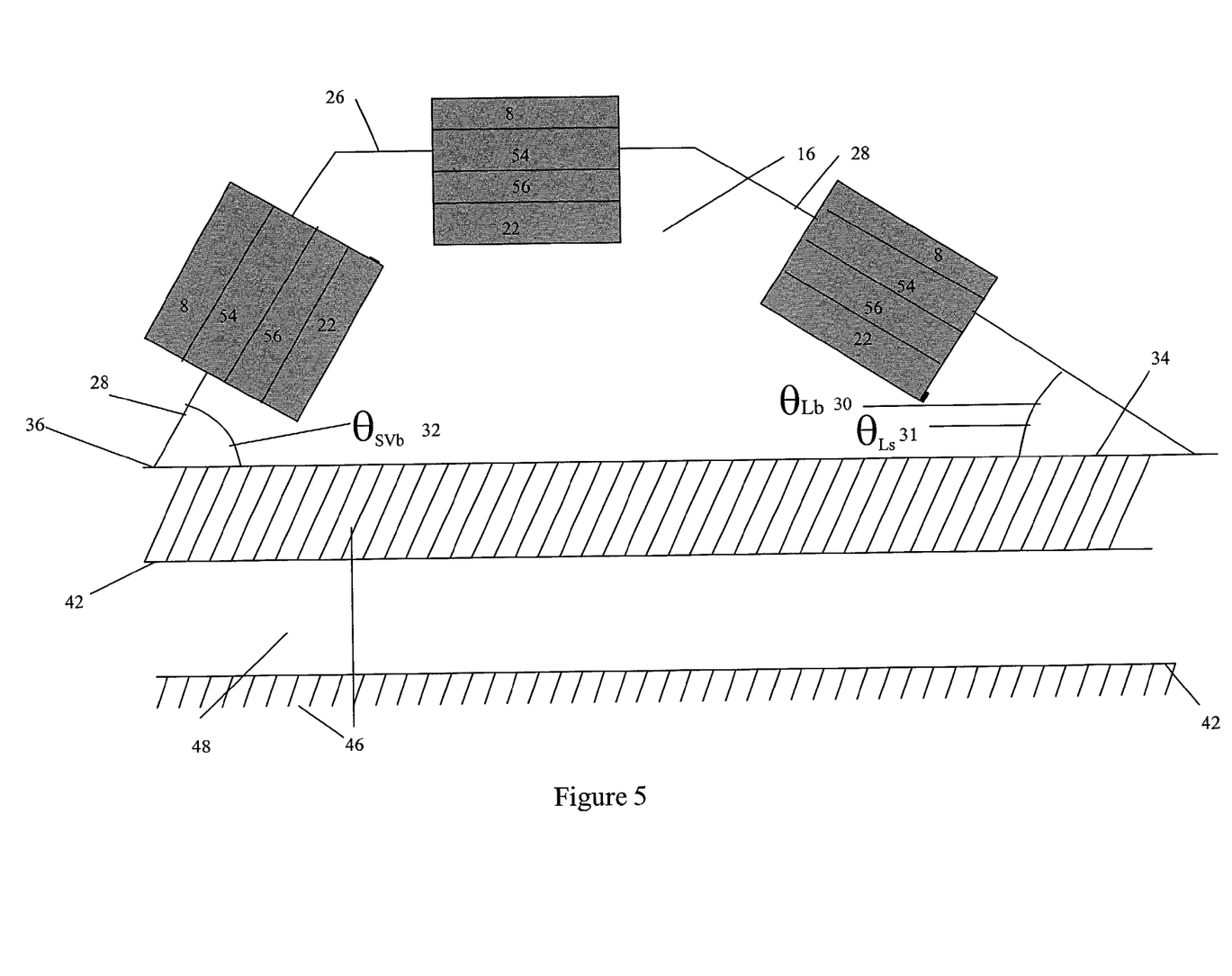
FIG. 5 is a cross-sectional view of one embodiment of the modal converter configured as an asymmetrical trapezoidal wedge which depicts the system controller, signal generator and transducer as units, with rechargeable batteries, integrated within the modal converter.

In the embodiments illustrated, the modal converter 16 is configured as an asymmetrical wedge having a trapezoidal cross-section capable of accurately positioning a plurality of transducers relative to the skin tissue surface 36. FIGS. 1 through 3 show a flat transducer 18, a first critical angled transducer 20, and a second critical angled transducer 22. Each transducer is constructed of materials and designs that are commonly used in ultrasound applications. The at least one transducer may have piezoelectric properties, which include, but are not limited to, ceramic, single-crystal relaxor ferroelectric, lead zirconate titanate, lead metaniobate, barium titanate, and piezoelectric co-polymers of polyvinylidene fluoride (PVDF). Alternatively, the transducer may have magnetostrictive properties. The transducers are typically mounted on the outer surface of the modal converter. However, the transducers may be mounted on the modal converter as an inset within cavities in the modal converter 16, or mounted inside the modal converter 16 itself, as shown in FIG. 5. Further, the transducers may be positioned on the modal converter in any manner which allows the transducers to emit ultrasonic acoustic waves in accordance with the angles set forth below. The transducers are acoustically coupled to the modal converter with a coupling material having an acoustic impedance comparable to the acoustic impedance of the modal converter, which is an acoustic impedance within plus or minus ten percent of the acoustic impedance of the modal converter. In some embodiments, the acoustic impedance of the modal converter is almost equal to that of human soft tissue. Additionally, the modal converter 16 is composed of materials having a longitudinal velocity that is less than the longitudinal velocity for human musculo-skeletal soft tissue and that is less than the longitudinal velocity for bone tissue. The acoustic waves which emanate from each of the transducers are controlled spatially and temporally by a system controller 24. The design and fabrication of the system controller 24 are well known to those who practice the art.

The modal converter 16 of FIGS. 1 through 3 includes a substantially flat top surface 26 and multiple angled surfaces 28. However, as shown in FIG. 5, if the transducers are inset within the modal converter 16, the top surface 26 need not be substantially flat. Instead, the top surface 26 may be any shape as long as the transducer 18 is parallel within the bottom surface 34 of the modal wedge converter 16. The transducer 18 positioned on the substantially flat top surface 26 or inset within the modal wedge converter 16 provides the treatment area 52 with longitudinal waves perpendicular to the skin tissue surface 36 and the bone tissue surface 42. The angled surfaces 28 are located at either a first-critical angle for bone tissue, $\theta_{Lb}$ 30 or for skin tissue, $\theta_{Ls}$ 31 or a second critical angle for bone tissue, $\theta_{SVb}$ 32. All critical angles specified are with respect to the bottom surface 34 of the modal converter 16.

In operation, the bottom surface 34 of the modal converter 16 is coupled to a skin tissue surface using a coupling material having an acoustic impedance comparable to the acoustic impedance for human soft tissue 36, thereby maximizing the transfer of acoustic energy from the modal converter 16 to the human body. The subscripts for the above angles, as indicated in FIGS. 1 to 3, denote (reading from left to right) the propagating acoustic mode, longitudinal (L) or vertical shear (SV), followed by the tissue surface along which the acoustic wave propagates after reflection at the respective interface, namely, bone (b) or skin (s).

The angled transducers 20 and 22 are capable of being located at numerous critical angles that enable the acoustic waves produced by the transducers to provide the various coupling paths as shown in FIGS. 1 through 3. For instance, the angled transducers 20 and 22, as depicted in FIG. 1, provide the treatment area 52 with longitudinal waves 40 and shear waves 44 that propagate parallel to and along the bone tissue surface 42. Further, the acoustic waves emitted by the angled transducers 20 and 22, as depicted in FIG. 2, may be converted into longitudinal waves 40 that propagate parallel to and along both the skin tissue surface 36 and bone tissue surface 42. Additionally, the angled transducers 20 and 22, as depicted in FIG. 3, can provide the treatment area 52 with longitudinal waves 40 that propagate parallel to and along the skin tissue surface 36 and shear waves 44 that propagate parallel to and along the bone tissue 42 surface.

A therapeutically desirable set of acoustic waves can be produced by locating the angled transducers 20 and 22 at certain critical angles. Specifically, the angled transducers 20 and 22 positioned at first critical angles, $\theta_{Lb}$ 30 and $\theta_{LS}$ 31, can produce longitudinal waves that travel parallel to and along the bone tissue 42 and skin tissue 36 surfaces, respectively. Further, the angled transducers 20 and 22 positioned at second critical angle, $\theta_{SVb}$ 32, can produce shear waves that travel parallel to and along the bone tissue 42. These critical angles $\theta_{Lb}$ 30, $\theta_{Ls}$ 31, and $\theta_{SVb}$ 32 may be calculated using relationships between the velocity of longitudinal and shear waves and the elastic properties of solid isotropic homogeneous bulk material, as set forth below. For common modal converter materials, $\theta_{Lb}$ 30 is less than $\theta_{SVb}$ 32 which is less than $\theta_{Ls}$ 31.

The reflection of an ultrasonic wave occurs at the interface between two media with different acoustic impedances. Two such locations are at the skin tissue surface 36 and bone tissue surface 42. The acoustic impedance is given in Rayls (kg/m²-sec) and, for longitudinal waves in bulk materials, is defined as $\rho C_L$, where $\rho$ is the mass density and $C_L$ is the longitudinal velocity of sound in a material. The strength of a reflected wave is determined by the reflection coefficient R at the interface between two media and, in terms of their acoustic impedances, $Z_1$ and $Z_2$, is given as $R=(Z_2-Z_1)/(Z_2+Z_1)$, which may produce a phase shift depending on the relative acoustic impedance of the media. Subscripts 1 and 2 refer to the first and second mediums, where the first medium is characterized by incidence and reflection and the second medium is characterized by refraction and transmission.

For the purposes of estimating the angles to treat bone tissue, the surrounding soft tissue 46 and bone tissue 48 can be considered to be solid isotropic homogeneous material. As such, the longitudinal velocity of the acoustic waves can be expressed in terms of the elastic properties of the tissues:

$$C_L = \{(E/\rho)[(1-v)/(1+v)(1-2v)]\},$$

where E is Young's modulus, $\rho$ is the density, and $\sigma$ is Poisson's ratio, which is a function of the ratio of the shear-to-longitudinal wave velocities. Specifically, Poisson's ratio is calculated as $v=[1-2(C_s/C_L)^2]/2[1-(C_s/C_L)^2]$, where $C_s$ is the shear wave velocity of acoustic waves.

The particle direction of shear waves 44 is normal to the propagation direction and may be more effective than longitudinal waves in stimulating the periosteum and surrounding soft tissue found near and at the bone fracture site. There exist two types of shear waves 44, namely shear horizontal and shear vertical which are designated SH and SV, respectively, depending upon the direction of particle movement with respect to the propagation direction. In general, a random shear wave incident at a boundary between two different solid media contains both SH and SV components. Further, SV waves can undergo modal conversion according to the boundary condition established by Snell's Law:

$$(\sin \theta_S/C_s)_1 = (\sin \theta_L/C_L)_1 = (\sin \theta_L/C_L)_2 = (\sin \theta_S/C_S)_2 \qquad \text{equation 1,}$$

where $\theta_S$ is the shear angle, $\theta_L$ is the longitudinal angle, $C_S$ is the shear velocity, and $C_L$ is the longitudinal velocity. This boundary condition defined by Snell's law also describes the interaction of the longitudinal wave at the interface between medium 1 and medium 2. In contrast, SH waves cannot undergo modal conversion. Instead, SH waves maintain motion that is parallel to the boundary. An acoustic waveguide, such as a bone fracture channel, can support pure SH waves.

When longitudinal waves are directed to reflection site 50 by a modal converter having a first critical angle $\theta_{Lb}$ 30 or $\theta_{Ls}$ 31 that produce angles of refraction at the bone or skin tissue surface of 90 degrees, the refracted longitudinal waves travel parallel to the interface between bone tissue 48 and the surrounding soft tissue 46 or travel parallel to the interface between the bottom of the modal converter 34 and the skin tissue surface 36. If the angle of incidence is greater than the critical angle, the sine of the angle of refraction as computed by Snell's law is greater than unity. In other words, once the angle of incidence becomes greater than the critical angle, the acoustic wave does not pass into the second medium; rather, it is totally reflected internally at the boundary surface. For angles of incidence that are much greater than the critical angle, the amplitude of the longitudinal wave at the surface, although finite, has very little real acoustic power. Note, too, that there cannot exist a refracted critical angle when the sound velocity in the first medium is less than the sound velocity in the second medium. When a longitudinal wave is transmitted in medium 1 at the first critical angle for a specified boundary surface, the refracted shear wave in medium 2 is at the angle $\theta_{SV2}$ given by:

$$\theta_{SV2} = \sin^{-1}\{(1-2v)/2(1-v)\}^{1/2}, \qquad \text{equation 2,}$$

where $v$ is Poisson's ratio for bone tissue or soft tissue. Poisson's ratio for all materials ranges between 0 and 0.5, where materials with $v$ equal to 0 are termed completely compressible while materials with $v$ equal to 0.5 are termed incompressible. In particular, Poisson's ratio for bone tissue is typically within the range from about 0.29 to about 0.33, while Poisson's ratio for human soft tissue and most elastomers and thermoplastics is typically from about 0.45 to about 0.49. For v ranging between about 0.29 and about 0.33 and between about 0.45 and about 0.49, $C_S/C_L$ ranges between about 0.5 and about 0.54 and between about 0.14 and about 0.3, respectively. From this data, the modal converter and musculo-skeletal soft tissue can be modeled as a quasi viscous fluid and bone tissue can be modeled as a quasi viscoelastic solid.

As depicted in FIGS. 1 and 3, when longitudinal waves are directed to the reflection site 50 at the critical angle $\theta_{SVb}$ 32, the reflected longitudinal waves at the skin tissue surface are negligible and only the refracted shear waves exist in the soft tissue. For the condition when $\theta_{SVb}$ equals 90 degrees in bone tissue, the longitudinal waves are converted completely into shear waves that travel parallel to the bone tissue surface 42. As the angle for $\theta_{SVb}$ 32, created between angled surface 28 and bottom surface 34 of the modal wedge converter 16, is increased and consequently $\theta_{SVb}$ approaches $\theta_{Ls}$, the acoustic longitudinal waves tend toward propagating along the skin tissue interface while the shear wave reflected from the bone surface becomes negligible, decaying exponentially from the bone surface.

The first critical angle 30 and the second critical angle 32 may be established using equation 1 set forth above. According to *Measurement of Velocity and Attenuation of Shear Waves in Bovine Compact Bone Using Ultrasonic Spectroscopy* that was written by Wu and Cubberley and published in Ultrasound in Med. & Biol., Vol. 23, No. 1, 129-134, 1997, the average longitudinal velocity in bone tissue has been measured in vitro as being within a range from about 3075 to about 3350 meters per second (m/s), depending on the direction of the acoustic wave relative to the length of the bone fiber. In the same experiment, the average shear wave velocity in bone tissue has been measured to be from about 1750 to about 1950 m/s. These velocities were used in calculation of $\theta_L$ and $\theta_{SV}$ in equation 1 set forth above for various modal converter materials. The ranges of angles for $\theta_{Lb}$ 30, $\theta_{Ls}$ 31, and $\theta_{SVb}$ 32 are given in the following table for various materials whose acoustic impedance is within 10 percent of the acoustic impedance for soft tissue:

| Acoustic Modes | Modal Converter Materials | Range of Critical Angles (Degrees) |
|---|---|---|
| Longitudinal Waves Along Bone Surface (Lb) | Thermoplastics | 26-30 |
| Longitudinal Waves Along Bone Surface (Lb) | RTV Elastomer (Rubber) | 14-21 |
| Longitudinal Waves Along Skin Surface (Ls) | Thermoplastics | 74-77 |
| Longitudinal Waves Along Skin Surface (Ls) | RTV Elastomer (Rubber) | 31-43 |
| Shear Waves Along Bone Surface (SVb) | Thermoplastics | 50-60 |
| Shear Waves Along Bone Surface (SVb) | RTV Elastomer (Rubber) | 25-38 |

The nominal properties of the materials involved in the calculation of the critical angles, $\theta_{Lb}$ 30, $\theta_{Ls}$ 31, and $\theta_{SVb}$ 32, include:

| Material | Z (MRayl) | $C_L$ (m/s) | $C_{SV}$ (m/s) |
|---|---|---|---|
| Transducer (PZT) | 28-32 | 3800 | |
| Matching Layer | 4.4-4.9 | 2800 | |
| Thermoplastics | 1.56-1.63 | 1500-1520 | 210-460 |
| RTV family | 1.41-1.55 | 830-1080 | 115-325 |
| Bone Tissue | 6.8 | 3075-3350 | 1750-1950 |
| Soft Tissue | 1.4-1.68 | 1444-1570 | 220-470 |

The values for $C_{SV}$ are based on the range of Poisson's ratio for the various materials given above. Shear velocities for several types of mammalian tissue have been measured in vitro to be less than 20 meters per second, which is more than an order of magnitude less than the range of values shown in the above table for $C_{SV}$ and indicates a Poisson's ratio greater than 0.4995.

In the modal converter 16, transducers are positioned so that acoustic waves may be transmitted to the treatment area 52 in numerous ways. For instance, an acoustic longitudinal wave may propagate to the bone fracture site as an incident longitudinal wave 40 normal to the skin tissue surface 36 and the bone surface 42. In another example, an acoustic longitudinal wave may be transmitted at an angle equal to the first critical angle, $\theta_{Lb}$ 30, which after incidence at the interface between surrounding soft tissue 46 and bone tissue 48 is converted partially into a longitudinal wave 40 that travels along the surface of the bone 42 and partially into a shear wave that travels at a refracted angle given by equation 2. For this condition, the refracted angle of shear waves in bone tissue ranges from about 30 to 33 degrees. In yet another example, an acoustic longitudinal wave may be transmitted at an angle equal to the second critical angle, $\theta_{SVb}$ 32 which again, after incidence at the interface between surrounding soft tissue and bone tissue, is totally converted into a SV shear wave 44 that travels along the interface between surrounding soft tissue and bone tissue. And in still yet another example, an acoustic longitudinal wave may be transmitted at an angle equal to the first critical angle, $\theta_{Ls}$ 31, which after incidence at the skin tissue surface 36, is converted partially into a longitudinal wave 40 that travels along the surface of the skin 36 and partially into a shear wave that travels at a refracted angle in the underlying soft tissue 46 given by equation 2. For this condition, the refracted angle of shear waves in the soft tissue 46 may range from about 0 to about 18 degrees. These refracted shear waves may have considerable therapeutic value in promoting skin tissue wound healing.

The configuration of modal converter 16 establishes the proper alignment of the transducers with respect to the bone tissue surface 42 in order to produce the desired incidence angle $\theta_{Lb}$ 30, $\theta_{Ls}$ 31, or $\theta_{SVb}$ 32 for the desired acoustic modes within the treatment area 52, as shown in FIGS. 1 through 3. In various embodiments, the modal converter may include one or more of these and other modes.

Ultrasound wave propagation in tissue exerts a unidirectional radiation force on all absorbing and reflecting obstacles in its path, even at the microstructural level. In embodiments of this invention, the acoustic waves in the soft tissue 46 are characterized as a low spatial average-temporal average (SATA) acoustic intensity, typically 30 to 100 mW/cm². This level of acoustic waves just exceeds the biological thresholds which can trigger or invoke a cascade of biological healing mechanisms. Further, the therapeutic carrier frequency can range from 10 kHz to 10 MHz. Control of both the absorbing and reflecting paths in tissue can result in significant therapeutic benefits.

In operation, the modal converter 16 is placed on the skin tissue surface 36 of a patient over a treatment area 52 which may be composed of an open tissue wound or a bone fracture site, or both. For an open wound, an ultrasound couplant sheet, such as Hydroscan available from Echo Ultrasound (Reedsville, Pa.), can be placed over the wound for sterile protection and to reduce cross contamination. The modal converter 16 positions at least one transducer with respect to the skin tissue surface 36 between the bottom of the modal converter 34 and the soft tissue 46, and with respect to the bone surface interface 42 between the surrounding soft tissue 46 and the bone tissue 48. Interrogation of the treatment area 52 is initiated by actuating the system controller 54. The system controller 54 triggers a programmable signal generator 56 to produce ultrasonic excitation signals that are sent to one or more transducers. Each transducer receiving an excitation signal emits an acoustic longitudinal wave that propagates through the modal converter material 16, the skin tissue surface 36 and surrounding soft tissue 46, toward the bone tissue 48. The modal converter 16 may also be used to transmit acoustic waves toward a wound on a skin tissue surface 36 which does not include bone tissue. As set forth above, the acoustic longitudinal wave may undergo modal conversion, depending on the angle of incidence at which the acoustic wave strikes the bone tissue surface 42.

The at least one transducer produces specific sequential or simultaneous transmissions of acoustic waves, which is controlled by the system controller 54, in order to noninvasively interrogate the treatment area 52 ultrasonically. The system controller 54 may be a programmable microprocessor, but may also include, though is not limited to, integrated circuits, analog devices, programmable logic devices, personal computers or servers. The timing sequences may be established by the user at any time or established during the manufacturing process. In some embodiments, the modal converter 16 may be used to administer therapeutic treatment composed of an ultrasound dosage administered once or twice a day, and repeated daily for several months to effectively stimulate the healing process. In some embodiments, one dosage of acoustic waves ranges between 1 and 60 minutes in length for one or more of the transducers. The modal converter 16 may be used to facilitate and enhance application of therapeutic ultrasound dosages to shallow or deep anatomical structures, or both, in an effort to expedite tissue wound healing, including both the endostial and periostial healing phases in the bone fracture healing process.

Figure 4:
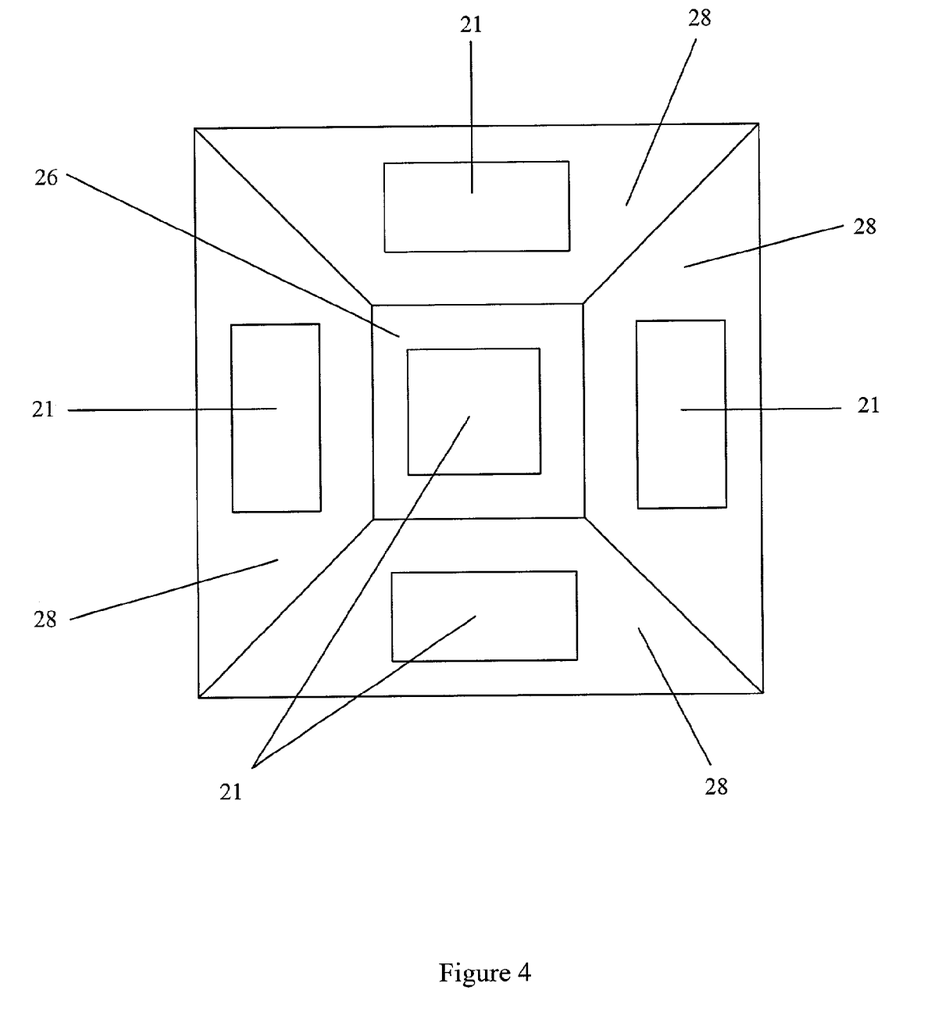
FIG. 4 is a top plan view of an embodiment of the present invention in which four transducers are mounted on angled sides of the modal converter and one transducer is mounted on the top surface of the modal converter.

In some embodiments, the modal converter 16 includes three transducers, as illustrated in FIGS. 1 through 3. However, in an alternative embodiment as shown in FIG. 4, the modal converter 16 may also include a flat surface 26 and four angled surfaces 28. In the alternative embodiment, one transducer 21 is located on the flat top surface 26 and at least one transducer 21 is located on at least one of the four angled surfaces 28. Each of these angled surfaces 28 may be positioned at either the first critical angle, $\theta_{Lb}$ 30 or $\theta_{Ls}$ 31, or the second critical angle, $\theta_{SVb}$ 32. Further, all four angled surfaces 28 may all be located at the first critical angle, $\theta_{Lb}$ 30 or $\theta_{Ls}$ 31. Alternatively, all four angled surfaces 28 may be located at the second critical angle $\theta_{SVb}$ 32. Further embodiments could include any combination of angled surfaces 28 at critical angles, $\theta_{Lb}$ 30, $\theta_{Ls}$ 31 or $\theta_{SVb}$ 32.

Further, another alternative embodiment may include more than five transducers. For instance, the modal converter 16 may include a flat top surface 26 as shown in the alternative embodiment depicted in FIG. 4. However, rather than limiting the number of sides to four, this alternative embodiment may include a plurality of angled sides greater than four in number. Specifically, the angled surfaces 28 could be any number greater than four. Further, the angled surfaces 28 may be any combination of sides having angles located either at $\theta_{Lb}$ 30, $\theta_{Ls}$ 31 or at $\theta_{SVb}$ 32.

In some embodiments, a single transducer 18 is located on the flat top surface 26 as shown in FIGS. 1 through 3 and at least one transducer is located on an angled surface 28 of the modal converter 16. However, in an alternative embodiment, each angled surface 28 may include an array of transducers, rather than a single transducer. The array of transducers may include any number of transducers greater than one. Further, alternative embodiments may include only one angled surface having an array of transducers that may or may not include a top surface having an array of transducers. Additionally, any combination of arrays herein described may be included within any of the embodiments set forth above. In still another embodiment, the modal converter may have only a top flat surface 26, with or without angled sides, where the array of transducers on the top surface 26 is electronically phased to form a beam which can be steered electrically to the critical angles $\theta_{Lb}$ 30, $\theta_{Ls}$ 31 or $\theta_{SVb}$ 32. The method of electrically steering an acoustic beam is well known to those who practice the art.

As a further extension of these embodiments, the system controller 54 may be programmed to apply therapeutic ultrasound dosages through any combination of described modal converters in order to target various tissue wounds and bone fracture sites in a patient. Additionally, the system controller 54, the programmable signal generator 56 and the transducers 18, 20, and 22 may be included within a single integrated unit. In this embodiment, each unit may be separately mounted on at least one of the plurality of surfaces of the modal converter, mounted as in inset, or mounted inside the modal converter itself, as shown in FIG. 4, as a standalone unit with rechargeable batteries 58. Thus, the modal converter could house the transducers 18, 20 and 22, the system controller 54, and the programmable signal generator 56 within a single structure. Further, the integrated standalone units shown in FIG. 5 could also be electrically connected to a single external power source.

In any of the previously described embodiments, the plurality of transducers may be programmed with different ultrasonic excitation signals, characterized by amplitude or phase modulation, or both, and by varying the carrier frequency, pulsewidth, pulse repetition frequency, and spatial-average temporal-average (SATA) intensity, such as those described and schematically depicted in U.S. Pat. No. 5,520,612 to Winder et al., which is hereby incorporated by reference. The carrier frequency may be between about 10 kHz and about 10 MHz for one or more of the transducers. The pulsewidth may be within the range from about 100 microseconds to about 100 milliseconds for one or more of the transducers. The pulse repetition frequency may be within the range from about 1 Hz to about 10,000 Hz. The spatial-average temporal-average intensity may be within the range from about 5 mW/cm$^2$ to about 500 mW/cm$^2$ for one or more of the transducers. The degree of amplitude modulation is defined by the modulation index, which may be within the range from about 0 to about 0.5 for one or more transducers. The phase modulation is defined by the linear or nonlinear frequency versus time characteristic. Typically, the phase modulation may range from a delayed linear (CW) to logarithmic (hyperbolic FM) variation, where the frequency versus time characteristic f(t) is represented by an infinite power series in time given as:

$$f(t) = \alpha_0 + \alpha_1 t + \alpha_2 t^2 + \alpha_3 t^3 + \quad \text{equation 3,}$$

where the set of constants [α] characterize the particular modulation system.

Various embodiments of this invention have been set forth above, including descriptions of specific embodiments given for purposes of illustration and explanation. Variations, changes, modifications, and departures from the systems and methods disclosed above may be adopted without departure from the spirit and scope of this invention.

We claim:

1. A method of noninvasively applying an ultrasonic excitation signal from at least one transducer to human tissue in vivo for therapeutic applications, comprising:
    acoustically coupling a modal converter to a tissue surface, wherein the modal converter comprises a top surface, a bottom surface, and a plurality of side surfaces positioned at angles relative to the bottom surface such that the at least one transducer is acoustically coupled to one of the plurality of side surfaces and can emit an acoustic wave that reflects at an interface, and after reflection, travels parallel to and along the interface; and
    emitting an acoustic wave from the at least one transducer acoustically coupled to the modal converter at an angle relative to the bottom surface of the modal converter, such that the acoustic wave emitted from the at least one transducer reflects upon striking the interface and after reflection travels parallel to and along the interface, whereby said acoustic wave impinges and has a therapeutic effect on organic tissue.

2. The method of claim 1, further comprising generating an excitation signal and transmitting the excitation signal to the at least one transducer.

3. The method of claim 2, wherein generating an excitation signal further comprises generating an excitation signal that is a modulated pulsed sine wave.

4. The method of claim 3, wherein generating an excitation signal further comprises generating an excitation signal that is amplitude modulated.

5. The method of claim 3, wherein generating an excitation signal further comprises generating an excitation signal that is phase modulated.

6. The method of claim 5, wherein generating an excitation signal further comprises generating an excitation signal that is within the range from a delayed linear (CW) to a logarithmic (hyperbolic FM) variation with time, based on a power series representation of a frequency versus time curve as defined by $f(t)=a_o+a_1 t+a_2 t^2+a_3 t^r+\ldots$, wherein the set of constants, a, characterize a particular modulation system.

7. The method of claim 3, wherein generating an excitation signal further comprises generating an excitation signal comprising a carrier frequency, a pulsewidth, a pulse repetition frequency, and a spatial-average temporal-average intensity.

8. The method of claim 7, wherein generating an excitation signal further comprises generating an excitation signal comprising a carrier frequency that is within the range of 10 kHz to 10 MHz for the at least one transducer.

9. The method of claim 7, wherein generating an excitation signal further comprises generating an excitation signal comprising a pulsewidth that is within the range of 100 microseconds to 100 milliseconds for the at least one transducer.

10. The method of claim 7, wherein generating an excitation signal further comprises generating an excitation signal comprising a pulse repetition frequency that is within the range of 1 Hz to 10,000 Hz for the at least one transducer.

11. The method of claim 7, wherein generating an excitation signal further comprises generating an excitation signal comprising a spatial-average temporal-average intensity that is within the range of 5 mW/cm² to 500 mW/cm² for the at least one transducer.

12. The method of claim 1, further comprising controlling the spatial and temporal distribution of acoustic energy from the at least one transducer using a system controller.

13. The method of claim 12, wherein using the system controller further comprises using a programmable microprocessor.

14. The method of claim 1, further comprising generating longitudinal waves that propagate substantially normal to the tissue surface, the waves being generated from at least one transducer positioned on the top surface of the modal converter.

15. The method of claim 1, wherein emitting an acoustic wave toward the interface further comprises emitting the acoustic wave toward an interface between a skin tissue surface and the modal converter.

16. The method of claim 15, wherein emitting the acoustic wave toward an interface between a skin tissue surface and the modal converter further comprises emitting the acoustic wave at a first critical angle relative to the bottom surface of the modal converter such that the acoustic wave converts partially into a longitudinal wave traveling parallel to and along the skin tissue surface, and converts partially into a shear wave traveling at a refraction angle, $\theta_{sv}$, after incidence at the interface between the skin tissue surface and the modal converter, wherein $\theta_{sv}=\sin^{-1}\{(1-2v)/2(1-v)\}^{1/2}$, wherein v represents Poisson's ratio for soft tissue and sv refers to the vertical component of the shear wave.

17. The method of claim 1, wherein emitting the acoustic wave toward the interface further comprises emitting the acoustic wave toward an interface between bone tissue and surrounding soft tissue.

18. The method of claim 17, wherein emitting the acoustic wave toward an interface between bone tissue and surrounding soft tissue further comprises emitting the acoustic wave at a first critical angle relative to the bottom surface of the modal converter such that the acoustic wave converts partially into a longitudinal wave traveling parallel to and along the interface between the surrounding soft tissue and the bone tissue, and converts partially into a shear wave traveling at a refraction angle, $\theta_{sv}$, after incidence at the interface between the surrounding soft tissue and the bone tissue, wherein $\theta_{sv}=\sin^{-1}\{(1-2v)/2(1-v)\}^{1/2}$, wherein v represents Poisson's ratio for bone tissue and sv refers to the vertical component of the shear wave.

19. The method of claim 18, further comprising emitting an acoustic wave from the at least one transducer at a second critical angle relative to the bottom surface of the modal converter such that the acoustic wave reflects and travels as an acoustic shear wave parallel to and along the interface between the surrounding soft tissue and bone tissue after incidence at the interface between the surrounding soft tissue and bone tissue.

20. The method of claim 19, further comprising emitting an acoustic wave from the at least one transducer at the second critical angle that converts totally into an acoustic shear wave traveling parallel to and along the bone tissue surface.

21. The method of claim 1, wherein acoustically coupling a modal converter to a tissue surface further comprises acoustically coupling a modal converter comprising a material having an acoustic impedance comparable to an acoustic impedance for human soft tissue.

22. The method of claim 1, wherein acoustically coupling a modal converter to a tissue surface further comprises acoustically coupling a modal converter comprising a material having a longitudinal velocity less than a longitudinal velocity for human soft tissue.

23. The method of claim 1, wherein acoustically coupling a modal converter to a tissue surface further comprises acoustically coupling a modal converter comprising a material having a longitudinal velocity less than a longitudinal velocity for bone tissue.

24. The method of claim 1, wherein acoustically coupling a modal converter to a tissue surface further comprises acoustically coupling a modal converter comprising thermoplastics, thermosets, elastomers or combinations thereof.

25. The method of claim 24, wherein acoustically coupling a modal converter to a tissue surface further comprises acoustically coupling a modal converter comprising ethyl vinyl acetate, ecothane, polyurethane, silicone or combinations thereof.

26. The method of claim 1, wherein acoustically coupling a modal converter to a tissue surface further comprises acoustically coupling a modal converter comprising a coupling material having an acoustic impedance comparable to an acoustic impedance for human soft tissue.

27. The method of claim 1, wherein the emitting of acoustic waves from the at least one transducer occurs multiple times during a time period comprising a dosage period, wherein the dosage period is between about 1 and about 60 minutes.

28. An apparatus for noninvasively applying an ultrasound excitation signal from at least one transducer to human tissue in vivo for therapeutic applications, comprising:
a modal converter including a top surface, a plurality of side surfaces, a bottom surface parallel to the top surface, and a plurality of ultrasonic transducers, wherein the plurality of side surfaces are positioned at angles relative to the bottom surface and wherein a first ultrasonic transducer is acoustically coupled with the top surface and a second ultrasonic transducer is acoustically coupled to at least one of the plurality of sides of the modal converter and is positioned relative to the bottom surface, such that an acoustic wave emitted from at least one ultrasonic transducer strikes an interface, whereby said acoustic wave impinges and has a therapeutic effect on organic tissue.

29. The apparatus of claim 28, further comprising a system controller for controlling the spatial and temporal distribution of the acoustic wave from the at least one transducer.

30. The method of claim 29, wherein the system controller is a programmable microprocessor.

31. The apparatus of claim 28, further comprising a system generator for generating and transmitting an excitation signal to the at least one transducer.

32. The apparatus of claim 28, wherein said modal converter further comprises at least one transducer positioned on the top surface of the modal converter for generating longitudinal waves normal to the skin tissue surface.

33. The apparatus of claim 28, wherein the interface comprises an interface between a skin tissue surface and the modal converter.

34. The apparatus of claim 33, wherein at least one of the ultrasonic transducers is positioned at a first critical angle relative to the bottom surface and acoustically coupled to the at least one a plurality of sides of the modal converter so that the at least one transducer may emit an acoustic wave that converts partially into a longitudinal wave traveling parallel to and along the skin tissue surface and converts partially into a shear wave traveling at a refraction angle, $\theta_{sv}$, after incidence at the interface between the skin tissue surface and the modal converter, wherein $\theta_{sv}=\sin^{-1}\{(1-2v)/2(1-v)\}^{1/2}$, wherein v represents Poisson's ratio for human soft tissue and sv refers to the vertical component of the shear wave.

35. The apparatus of claim 34, wherein the at least one transducer is positioned at a first critical angle relative to the bottom surface and acoustically coupled to the at least one of a plurality of sides of the modal converter so that the at least one transducer may emit an acoustic wave that converts partially into a longitudinal wave traveling parallel to and along the interface between surrounding soft tissue and bone tissue and converts partially into a shear wave traveling at a refraction angle, $\theta_{sv}$, after incidence at the interface between surrounding soft tissue and bone tissue, wherein $\theta_{sv}=\sin-1\{(1-2v)/2(1-v)\}^{12}$, wherein v represents Poisson's ratio for human soft tissue and sv refers to the vertical component of the shear wave.

36. The apparatus of claim 28, wherein the interface comprises an interface between surrounding soft tissue and bone tissue.

37. The apparatus of claim 28, wherein the at least one transducer is positioned at a second critical angle relative to the bottom surface and acoustically coupled to the at least one of a plurality of sides of the modal converter such that the at least one transducer can emit an acoustic wave that reflects at the interface between the surrounding soft tissue and the bone tissue, and after incidence travels as an acoustic shear wave parallel to and along the interface between the surrounding soft tissue and the bone tissue.

38. The apparatus of claim 37, wherein the acoustic wave emitted from the at least one transducer at the second critical angle converts totally into an acoustic shear wave traveling parallel to and along the interface between the surrounding soft tissue and the bone tissue.

39. The apparatus of claim 28, wherein said modal converter comprises a material having an acoustic impedance comparable to an acoustic impedance for human soft tissue.

40. The apparatus of claim 28, wherein said modal converter comprises a material having a longitudinal velocity less than a longitudinal velocity for soft tissue.

41. The apparatus of claim 28, wherein said modal converter comprises a material having a longitudinal velocity less than a longitudinal velocity for bone tissue.

42. The apparatus of claim 28, wherein said modal converter comprises thermoplastics, elastomers or combinations thereof.

43. The apparatus of claim 42, wherein said modal converter further comprises ethyl vinyl acetate, ecothane, polyurethane, silicone or combinations thereof.

44. The apparatus of claim 28, wherein said modal converter further comprises the at least one transducer acoustically coupled to the top surface such that one acoustic wave emitted form the transducer is longitudinal and propagates substantially normal to the human tissue interface.

45. The apparatus of claim 28, wherein said modal converter comprises the at least one transducer positioned at an angle relative to the bottom surface such that one acoustic wave emitted from the at least one transducer reflects upon striking a human tissue interface and travels parallel to and along the human tissue interface.

46. A modal converter, comprising:
a top surface capable of receiving a first transducer;
a substantially flat bottom surface parallel to the top;
a plurality of side surfaces capable of receiving at least one second transducer and positioned at critical angles relative to the bottom surface wherein said top surface, said bottom surface and said plurality of side surfaces are adapted such that a therapeutic acoustic wave emitted from at least one of the first and second transducers strikes a human tissue interface, said acoustic wave impinges and has a therapeutic effect on said human tissue.

47. The modal converter of claim 46, wherein said modal converter further comprises a trapezoidal cross-section.

48. The modal converter of claim 46, wherein at least one side surface is positioned at a first critical angle relative to the bottom surface of the modal converter so that at least one of the ultrasonic transducers acoustically coupled to the at least one side surface can emit an acoustic wave that converts partially into a longitudinal wave traveling parallel to and along a skin tissue surface and converts partially into a shear wave traveling at a refraction angle, $\theta_{sv}$, after incidence at an interface between the skin tissue surface and the modal converter, wherein $\theta_{sv}=\sin^{-1}\{(1-2v)/2(1-v)\}^{1/2}$, wherein v represents Poisson's ratio for human soft tissue and sv refers to the vertical component of the shear wave.

49. The modal converter of claim 46, wherein at least one side surface is positioned at a first critical angle relative to the bottom surface of the modal converter so that at least one of the ultrasonic transducers acoustically coupled to the at least one side surface can emit an acoustic wave that converts partially into a longitudinal wave traveling parallel to and along an interface between surrounding soft tissue and bone tissue and converts partially into a shear wave traveling at a refraction angle, $\theta_{sv}$, after incidence at the interface between surrounding soft tissue and bone tissue, wherein $\theta_{sv}=\sin-1\{(1-2v)/2(1-v)\}^{1/2}$, wherein v represents Poisson's ratio for human soft tissue and sv refers to the vertical component of the shear wave.

50. The modal converter of claim 49, wherein at least one side surface is positioned at a second critical angle relative to the bottom surface of the modal converter such that at least one transducer acoustically coupled to the at least one side surface can emit an acoustic wave that reflects at the interface between the surrounding soft tissue and the bone tissue, and after incidence travels as an acoustic shear wave parallel to and along the interface between the surrounding soft tissue and the bone tissue.

51. The modal converter of claim 50, wherein the at least one side surface is positioned at the second critical angle relative to the bottom surface of the modal converter such that an acoustic wave emitted from the at least one transducer acoustically coupled to the at least one side surface converts totally into an acoustic shear wave traveling parallel to and along the interface between the surrounding soft tissue and the bone tissue.

52. The modal converter of claim 46, wherein said modal converter comprises a material having an acoustic impedance comparable to an acoustic impedance for human soft tissue.

53. The modal converter of claim 46, wherein said modal converter comprises a material having a longitudinal velocity less than a longitudinal velocity for soft tissue.

54. The modal converter of claim 46, wherein said modal converter comprises a material having a longitudinal velocity less than a longitudinal velocity for bone tissue.

55. The modal converter of claim 46, wherein said modal converter comprises thermoplastics, elastomers or combinations thereof.

56. The modal converter of claim 55, wherein said modal converter further comprises ethyl vinyl acetate, ecothane, polyurethane, silicone or combinations thereof.

57. The modal converter of claim 46, wherein said modal converter further comprises the at least one transducer acoustically coupled to the top surface such that one acoustic wave emitted form the transducer is longitudinal and propagates substantially normal to the human tissue interface.

58. The modal converter of claim 46 wherein said modal converter further comprises the at least one transducer acoustically coupled to the at least one side surface at a critical angle to the bottom surface emitting an acoustic wave such that the acoustic wave reflects upon striking the human tissue interface, and after reflection travels parallel to and along the human tissue interface.

59. A modal converter, comprising:
a top surface;
a substantially flat bottom surface parallel to the top surface;
a plurality of side surfaces;
at least one cavity located with the top surface, wherein the at least one cavity is capable of receiving at least one transducer and wherein said at least one cavity comprises at least one flat surface capable being acoustically coupled to at least one transducer and positioned parallel to the bottom surface such that an acoustic wave emitted from at least one transducer acoustically coupled to the at least one flat surface strikes a human tissue interface and provides therapeutic treatment to the area struck at the interface; and
at least one cavity located within at least one side surface, wherein the at least one cavity is capable of receiving at least one transducer and wherein said at least one cavity comprises at least one flat surface capable being acoustically coupled to at least one transducer and positioned at a critical angle relative to the bottom surface such that an acoustic wave emitted from at least one transducer acoustically coupled to the at least one flat surface reflects upon striking an interface and travels parallel to and along the interface.

60. The modal converter of claim 59, wherein at least one flat surface is positioned at a first critical angle relative to the bottom surface of the modal converter so that at least one transducer acoustically coupled to the at least flat side surface can emit an acoustic wave that converts partially into a longitudinal wave traveling parallel to and along a skin tissue surface and converts partially into a shear wave traveling at a refraction angle, $\theta_{sv}$, after incidence at an interface between the skin tissue surface and the modal converter, wherein $\theta_{sv}=\sin^{-1}\{(1-2v)/2(1-v)\}^{1/2}$, wherein v represents Poisson's ratio for human soft tissue and sv refers to the vertical component of the shear wave.

61. The modal converter of claim 59, wherein at least on flat surface is positioned at a first critical angle relative to the bottom surface of the modal converter so that at least one transducer acoustically coupled to the at least one flat surface can emit an acoustic wave that converts partially into a longitudinal wave traveling parallel to and along an interface between surrounding soft tissue and bone tissue and converts partially into a shear wave traveling at a refraction angle, 0sv, after incidence at the interface between surrounding soft tissue and bone tissue, wherein 0sv=sin−1 $\{(1-2v)/2(1-v)\}v2$, wherein v represents Poisson's ratio for human soft tissue and sv refers to the vertical component of the shear wave.

62. The modal converter of claim 61, wherein at least one flat surface is positioned at a second critical angle relative to the bottom surface of the modal converter such that at least one transducer acoustically coupled to the at least one flat surface can emit an acoustic wave that reflects at the interface between the surrounding soft tissue and the bone tissue, and after incidence travels as an acoustic shear wave parallel to and along the interface between the surrounding soft tissue and the bone tissue.

63. The modal converter of claim 62, wherein the at least one flat surface is positioned at the second critical angle relative to the bottom surface of the modal converter such that an acoustic wave emitted from the at least one transducer acoustically coupled to the at least one flat surface converts totally into an acoustic shear wave traveling parallel to and along the interface between the surrounding soft tissue and the bone tissue.

64. The modal converter of claim 59, wherein said modal converter comprises a material having an acoustic impedance comparable to an acoustic impedance for human soft tissue.

65. The modal converter of claim 59, wherein said modal converter comprises a material having a longitudinal velocity less than a longitudinal velocity for soft tissue.

66. The modal converter of claim 59, wherein said modal converter comprises a material having a longitudinal velocity less than a longitudinal velocity for bone tissue.

67. The modal converter of claim 59, wherein said modal converter comprises thermoplastics, elastomers or combinations thereof.

68. The modal converter of claim 67, wherein said modal converter further comprises ethyl vinyl acetate, ecothane, polyurethane, silicone or combinations thereof.

69. An apparatus for systemically administering therapeutic ultrasound to a patient, comprising:
a system controller for controlling the spatial and temporal distribution of acoustic energy from at least one first transducer and at least one second transducer coupled to a modal wedge converter comprising, a top surface, a plurality of side surfaces, a bottom surface parallel to the top surface, and the at least one first and at least one second transducers, wherein the plurality of side surfaces are positioned at angles relative to the bottom surface and wherein the at least one first transducer is acoustically coupled with the top surface and the at least one second transducer is coupled with at least one of the plurality of sides of the nodal converter and positioned such that an acoustic wave emitted from one of the first and second transducers strikes an interface, whereby said acoustic wave impinges and has a therapeutic effect on organic tissue.

70. The apparatus of claim 69, wherein the system controller is a programmable microprocessor.

* * * * *